(12) United States Patent
Bull et al.

(10) Patent No.: US 10,675,461 B2
(45) Date of Patent: Jun. 9, 2020

(54) FUNCTIONAL ELECTRICAL STIMULATION

(71) Applicant: Imperial Innovations Limited, London (GB)

(72) Inventors: Anthony M J Bull, London (GB); Lance Rane, London (GB)

(73) Assignee: Imperial College Innovations Limited, London (GB)

(*) Notice: Subject to any disclaimer, the term of this patent is extended or adjusted under 35 U.S.C. 154(b) by 172 days.

(21) Appl. No.: 15/885,365

(22) Filed: Jan. 31, 2018

(65) Prior Publication Data
US 2018/0221658 A1 Aug. 9, 2018

Related U.S. Application Data

(60) Provisional application No. 62/453,395, filed on Feb. 1, 2017.

(51) Int. Cl.
*A61N 1/36* (2006.01)

(52) U.S. Cl.
CPC ..... *A61N 1/36003* (2013.01); *A61N 1/36021* (2013.01)

(58) Field of Classification Search
CPC .......... A61N 1/36003; A61N 1/36021
USPC .......................................................... 607/46
See application file for complete search history.

(56) References Cited

U.S. PATENT DOCUMENTS

| 5,628,722 A | 5/1997 | Solomonow et al. | |
| 8,155,745 B1* | 4/2012 | Merrill | A61N 1/3787 607/49 |
| 2007/0179561 A1* | 8/2007 | Embrey | A61N 1/36003 607/49 |
| 2010/0160987 A1* | 6/2010 | Simmons | A61H 1/0237 607/3 |
| 2011/0295339 A1* | 12/2011 | Carroll | A61N 1/0452 607/49 |

OTHER PUBLICATIONS

Andersen et al., "The anterior cruciate ligament does play a role in controlling axial rotation in the knee", Knee Surg, 1997, 5, pp. 145-149.

Ardestani et al., "How human gait responds to muscle impairment in total knee arthroplasty patients: Muscular compensastions and articular perturbations", Journal of Biomechanics, 2016, 49, pp. 1620-1633.

Azmi et al., "Activiation of biceps femorsis long head reduces tibiofemoral anterior shear force and tibial internal rotation torque in healthy subjects", PLoS One, 2018, 13(1): pp. e0190672.

Brandon et al., "Selective lateral muscle activation in moderate medial knee osteoarthritis subjects does not unload medial knee condyle", Journal of Biomechanics, 2014, 47, pp. 1409-1415.

Buchanan et al., "Neuromusculoskeletal Modeling: Estimation of Muscle Forces and Joint Moments and Movements From Measurements of Neural Command", J Appl Biomech, 2004, 20(4), pp. 367-395.

(Continued)

*Primary Examiner* — Brian T Gedeon
*Assistant Examiner* — Philip C Edwards
(74) *Attorney, Agent, or Firm* — Stradley Ronon Stevens & Young, LLP

(57) ABSTRACT

Methods of treatment of disorders of the knee, such as medial osteoarthritis and knee instability due to anterior cruciate ligament deficiency, are provided herein.

19 Claims, 11 Drawing Sheets

(56) References Cited

OTHER PUBLICATIONS

Crowninshield et al., "A Physiologically Based Criterion of Muscle Force Prediction in Locomotion", J Biomechanics, 1981, 14(11), pp. 793-801.
Duffell et al., "Comparasion of kinematic and kinetic parameters calculated using a cluster-based model and Vicon's plug-in gait", Proc IMechE Part H: J Engineering in Medicine, 2014, 228(2), pp. 206-210.
Dumas et al., "A 3D Generic Inverse Dynamic Method using Wrench Notation and Quaternion Algebra", Computer Methods in Biomechanics and Biomedical Engineering, 2004, 7(3), pp. 159-166.
Duthon et al., "Anatomy of the anterior cruciate ligament", Knee Surg Sports Traumatol Arthrosc, 2006, 14, pp. 204-213.
Hermens et al., "Development of recommendations for SEMG senors and sensor placement procedures", Journal of Electromyography and Kinesiology, 2000, 10, pp. 361-374.
Jonkers et al., "The complementary role of the plantarflexors, hamstrings and gluteus maximus in the control of stance limb stability during gait", Gait and Posture, 2003, 17, pp. 264-272.
Komura et al., "Evaluation of the influence of muscle deactivation on other muscles and joints during gait motion", Journal of Biomechanics, 2004, 37, 425-436.
Lynch et al., "Closed-Loop Control of Induced Muscle Contractions", IEEE Control Systems Magazine, 2008, pp. 40-50.
Manal et al., "A More Informed Evaluation of Medial Compartment Loading: the Combined Use of the Knee Adduction and Flexor Moments", Osteoarthritis Cartilage, 2015, 23(7), pp. 1107-1111.
Martin et al., "Functional Electrical Stimulation in Spinal Cord Injury: From Theory to Practice", Top Spinal Cord Inj Rehabil, 2012, 18(1), pp. 28-33.
Miyaxaki et al., "Dynamic load at baseline can predict radiographic disease progression in medial compartment knee osteoarthritis", Ann Rheum Dls, 2002, 61, pp. 617-622.
Noyes et al., "The Symptomatic Anterior Cruciate-Deficient Knee", The Journal of Bone and Joint Surgery, 1983, 65-A(2), pp. 154-162.
Schipplein et al., "Interaction Between Active and Passive Knee Stabilizers During Level Walking", Journal of Orthopaedic Research, 1991, 9, pp. 113-119.
Sharma et al., "Knee Adduction Moment, Serum Hyaluronan Level, and Disease Severity in Medial Tibiofemoral Osteoarthritis", Arthritis and Rheumatism, 1998, 41(7), pp. 1233-1240.
Thomas et al., "Compartmental Evaluations of Osteoarthritis of the Knee", Radiology, 1975, 116, pp. 585-594.
Thorp et al., "The biomechanical effects of focused muscle training on medial knee loads in OA of the knee: a pilot, proof of concept study", J Musculskelet Neuronal Interact, 2010, 10(2), pp. 166-173.
Winby et al., "Muscle and external load contribution to knee joint contact loads during normal gait", Journal of Biomechanics, 2009, 42, pp. 2294-2300.
Winter et al., "EMG profiles during normal human walking: stride-to-stride and inter-subject variability", Electroencephalography and clinical Neurophysiology, 1987, 67, pp. 402-411.
Yeh et al., "A Comparison of Numerical Integrating Algorithms by Trapezoidal, Lagrange, and Spine Approximation", Journal of Pharmacokinetics and Biopharmaceutics, 1978, 6(1), pp. 79-98.
Zhao et al., "Correlation between the Knee Adduction Torque and Medial Contact Force for a Variety of Gait Patterns", Journal of Orthopaedic Research, 2007, pp. 789-797.
Solomonow, M. "Sensory-Motor control of ligaments and associated neuromuscular disorders", Journal of Electromyography and Kinesiology, 2006, 16:549-567.

\* cited by examiner

FUNCTIONAL ELECTRICAL STIMULATION

CROSS-REFERENCE TO RELATED APPLICATIONS

This application claims priority to U.S. Application No. 62/453,395, filed Feb. 1, 2017, which is incorporated herein by reference in its entirety.

FIELD OF THE INVENTION

The present invention relates to methods of treatment of disorders of the knee via functional electrical stimulation (FES) of specific muscle groups in the leg during gait. Specifically, the present invention provides a method of treating medial knee joint pain by FES of one or more of the gluteus medius, biceps femoris or gastrocnemius in the affected leg. There is also provided a method for treating or preventing medial osteoarthritis of the knee. Furthermore, there is provided a method of treatment of knee instability due to anterior cruciate ligament deficiency, the method comprising FES of the biceps femoris in the affected leg during gait.

BACKGROUND TO THE INVENTION

Medial knee pain is a debilitating condition, often leading to significant disability in affected patients. It is particularly common in patients suffering from osteoarthritis (OA) of the knee.

There has been increasing recognition of a biomechanical basis for joint pathology in OA, and with this hope that a new generation of disease modifying therapies might follow. Of particular significance is the emergence of aberrant joint loading as driver of disease. During gait, the medial compartment of the tibiofemoral joint bears 2.5 times the load borne by the lateral compartment (Schipplein & Andriacchi *J Orthop Res.* 1991; 9(1):113-119), and is the usual site of manifestation of OA of the knee (Thomas et al. *Radiology* 1975; 116(3):585-594). Once OA is established, the external adduction moment (EAM) of the knee, a more readily determined correlate of the internally acting medial knee joint reaction force (JRF), has been shown to predict disease severity (Miyazaki et al. *Ann Rheum Dis.* 2002; 61(7); 617-622) and risk of progression (Sharma et al. *Age* 1998; 6(9):15), suggesting utility as a clinical marker for reduction.

Normal loading of the knee during gait and other activities of daily living involves significant tibial anterior shear and tibial internal rotation torque (Andersen & Dyhre-Poulsen *Knee Surg Sports Traumatol Arthrosc.* 1997; 5:145-149). The anterior cruciate ligament (ACL) is the primary restraint to anterior tibial translation (ATT) and a major secondary restraint to internal tibial rotation (Noyes et al. *J Bone Joint Surg Am.* 1983; 65(2):154-162) and thus ACL deficiency through sports trauma results in instability of the knee (Duthon et al. *Knee Surg Sports Traumatol Arthrosc.* 2006; 14(3):204-213).

Functional electrical stimulation (FES) is a non-invasive technology that induces muscle contraction via the application of a voltage gradient.

SUMMARY OF INVENTION

The present application provides a method of treating medial knee joint pain during gait in a patient in need thereof, the method comprising applying FES to one or more of the gluteus medius, biceps femoris or gastrocnemius during gait.

Preferably, the method comprises the following steps during gait:
a. applying functional electrical stimulation to one or more of the gluteus medius, biceps femoris or gastrocnemius of the leg in need of treatment prior to foot strike of the foot of the leg in need of treatment;
b. maintaining functional electrical stimulation to the muscle(s) stimulated in step (a) for the period of stance of the leg in need of treatment;
c. ceasing functional electrical stimulation of the muscle stimulated in step (a) at the end of the period of stance of the leg in need of treatment;
d. optionally repeating steps (a) to (c) in respect of the corresponding muscle(s) of the patient's other leg; and
e. repeating steps (a) to (d) for each stride of the patient.

In preferred embodiments, FES involves applying a current of up to 150 mA to the relevant muscle. More preferably, a current of from 5 to 80 mA is applied. In yet further preferred embodiments, a current of 5, 10, 15, 20, 25, 30, 35, 40, 45, 50, 55, 60, 65, 70, 75 or 80 mA is applied.

In certain preferred embodiments, the FES is applied to the gluteus medius. In other preferred embodiments the FES is applied to the biceps femoris, preferably to the long head of the biceps femoris. In yet further preferred embodiments, the FES is applied to the gastrocnemius, preferably the lateral gastrocnemius. In yet further preferred embodiments, FES is applied to multiple muscles selected from gluteus medius, biceps femoris or gastrocnemius.

Preferably, the patient is human. In other preferred embodiments, the patient suffers from osteoarthritis of the knee.

The present invention also provides a method of treating or preventing osteoarthritis of the knee joint in a patient in need thereof, the method comprising applying functional electrical stimulation to one or more of the gluteus medius, biceps femoris or gastrocnemius of the leg in need of treatment during gait.

Preferably, the method comprises the following steps during gait:
a. applying functional electrical stimulation to one or more of the gluteus medius, biceps femoris or gastrocnemius of the leg in need of treatment prior to foot strike of the foot of the leg in need of treatment;
b. maintaining functional electrical stimulation to the muscle(s) stimulated in step (a) for the period of stance of the leg in need of treatment;
c. ceasing functional electrical stimulation of the muscle stimulated in step (a) at the end of the period of stance of the leg in need of treatment;
d. optionally repeating steps (a) to (c) in respect of the corresponding muscle(s) of the patient's other leg; and
e. repeating steps (a) to (d) for each stride of the patient.

In preferred embodiments, FES involves applying a current of up to 150 mA to the relevant muscle. More preferably, a current of from 5 to 80 mA is applied. In yet further preferred embodiments, a current of 5, 10, 15, 20, 25, 30, 35, 40, 45, 50, 55, 60, 65, 70, 75 or 80 mA is applied.

In certain preferred embodiments, the functional electrical stimulation is applied to the gluteus medius. In other preferred embodiments the functional electrical stimulation is applied to the biceps femoris, preferably to the long head of the biceps femoris. In yet further preferred embodiments, the functional electrical stimulation is applied to the gastrocnemius, preferably the lateral gastrocnemius. In yet further preferred embodiments, functional electrical stimulation is applied to multiple muscles selected from gluteus medius, biceps femoris or gastrocnemius.

Preferably, the patient is human.

Also provided in the present application is a method of treating knee instability during gait in a patient with an anterior cruciate ligament deficiency, the method comprising applying during gait functional electrical stimulation to the biceps femoris of the leg or legs having an anterior cruciate ligament deficiency.

Preferably, the method comprises the following steps during gait:
a. applying functional electrical stimulation to the biceps femoris of the leg having an anterior cruciate ligament deficiency, prior to foot strike of the foot of said leg;
b. maintaining functional electrical stimulation to the biceps femoris for the stance period said leg;
c. ceasing functional electrical stimulation of the biceps femoris at the end of the stance period of said leg;
d. optionally repeating steps (a) to (c) in respect of the patient's other leg; and
e. repeating steps (a) to (d) for each stride of the patient.

Preferably, the patient is human.

DETAILED DESCRIPTION

The present invention provides a method of treating medial knee joint pain during gait based upon FES of the gluteus medius of the leg in need of treatment. Pain reduction is achieved via the reduction in medial knee joint loading, i.e., a reduction in the medial joint reaction force of the knee.

The method may alternatively involve FES of the biceps femoris of the leg in need of treatment, in particular the long head of the biceps femoris. Furthermore, the method may alternatively involve FES of the gastrocnemius in the leg in need of treatment, in particular the lateral gastrocnemius.

Preferably, the method comprises the following steps during gait:
a. applying functional electrical stimulation to one or more of the gluteus medius, biceps femoris or gastrocnemius of the leg in need of treatment prior to foot strike of the foot of the leg in need of treatment;
b. maintaining functional electrical stimulation to the muscle(s) stimulated in step (a) for the period of stance of the leg in need of treatment;
c. ceasing functional electrical stimulation of the muscle stimulated in step (a) at the end of the period of stance of the leg in need of treatment;
d. optionally repeating steps (a) to (c) in respect of the corresponding muscle(s) of the patient's other leg; and
e. repeating steps (a) to (d) for each stride of the patient.

It will be appreciated that the term "gait" in this context is intended to mean bipedal locomotion, including but not limited to walking, jogging and running. Furthermore, the term "foot strike" refers to the moment at which the foot initially contacts the ground during gait.

The phrase "the leg in need of treatment" refers to the leg of the patient in which pain relief is sought. In certain embodiments this will be only one leg, though in other embodiments it may be both of the patient's legs.

FES may be applied by any suitable method known in the art. Typically, FES will be delivered via electrodes affixed to the skin immediately adjacent to the muscle to be stimulated. Alternatively, the electrodes may be embedded within the muscle via suitable means. Gel electrodes are particularly preferred. The degree of FES applied may be varied on a patient-by-patient basis. Where both legs require treatment, the level of FES applied to each leg may be the same or may be different.

The present invention finds particular utility in the treatment of patients suffering from osteoarthritis of the knee. Furthermore, the present invention also provides a method of treatment of osteoarthritis of the knee, based upon the same FES method. In particular, it is contemplated that the method of treatment of OA described herein will be particularly beneficial in early OA, where the reduction in knee JRF will lead to reduced disease progression and an improved prognosis.

OA patients tend to suffer a number of muscular deficiencies, and it has been hypothesised that these might drive joint pathology through the initiation and perpetuation of aberrant loading. Accordingly, physiotherapy may work by favourably altering joint kinetics, mitigating pathological processes in articular cartilage and so helping to reduce disease severity and symptoms. Despite the fact that muscle strengthening forms one of the mainstays of treatment in the early stages of knee OA, the optimal choice of muscle targets for inclusion in physiotherapy routines remains contentious. Traditionally, routines have focussed on those muscles at close proximity to the knee joint, but this is an approach that lacks a firm biomechanical basis.

As the controllers of frontal-plane pelvic motion the muscles around the hip, particularly gluteus medius, play a major role in stabilisation of the pelvis during gait. Gluteus medius acts to limit contralateral pelvic drop during stance phase, a role that becomes readily apparent when its severe weakness manifests as the Trendelenburg gait. Patients with this clinical sign demonstrate a waddling walking motion, their torsos lurching towards the stance side with each step to compensate for the shift of bodily centre of mass that results from pelvic drop towards the swing leg In patients with OA of the knee, pelvic kinetics have been shown to be of specific relevance to outcomes, with greater hip abduction moments during gait protecting against progression of disease from baseline to 18 months. Moreover, there is evidence that strengthening routines incorporating the hip musculature produce additional benefits over conventional physiotherapy routines. In a recent proof of concept study, intensive therapy directed towards gluteus medius enabled subjects with knee OA to reduce the magnitude of the EAM by an average of 9%. The authors posited a feasible biomechanical basis for the reduction, hypothesising that decreased tilt of the pelvis in the frontal plane shifted the ground reaction force vector towards the stance leg (lateralising it), reducing the varus torque and thus the medial load acting at the knee.

The present inventors have demonstrated that FES of the gluteus medius during gait reduces the medial knee joint reaction force, suggesting the utility of this non-invasive method in the treatment of medial knee pain. Furthermore, the present inventors have also shown that FES of the biceps femoris, in particular the long head of the biceps femoris, and the gastrocnemius, in particular the lateral gastrocnemius, leads to a reduction in the medial knee joint reaction force. FES of these muscles during gait may also therefore lead to reduction in medial knee pain.

The present invention also contemplates the treatment of OA via the use of FES applied to one or more of the gluteus medius, biceps femoris or gastrocnemius during gait. Aberrant loading of the knee is a driver of disease progression in OA, meaning that reduction of the medial knee joint reaction force is therefore likely to halt disease progression, or at the very least lead to a reduction in disease progression. Since FES of the gluteus medius, biceps femoris or gastrocnemius during gait reduce the medial knee joint reaction force, the use of this method finds utility in the treatment or prevention of OA, in particular early OA.

FES of the knee also finds utility in the treatment of knee instability during gait in patients with anterior cruciate ligament deficiencies. In particular, FES of the biceps femoris in patients with anterior cruciate ligament deficiencies reduces tibiofemoral anterior shear force and tibial internal rotation torque, mitigating knee instability. The present inventors have demonstrated that FES of the biceps femoris during gait reduces the anterior shear force at the knee and reduces the knee internal rotation torque, confirming the utility of this non-invasive method in the treatment of ACL deficiency, or in the rehabilitation of a patient post ACL reconstruction surgery.

BRIEF DESCRIPTION OF DRAWINGS

FIG. 5, Panel C: Reduction in mediolateral component of GRF versus reduction in medial knee JRF (R=0.88, p<0.0001)

EXAMPLE 1

Figure 1:
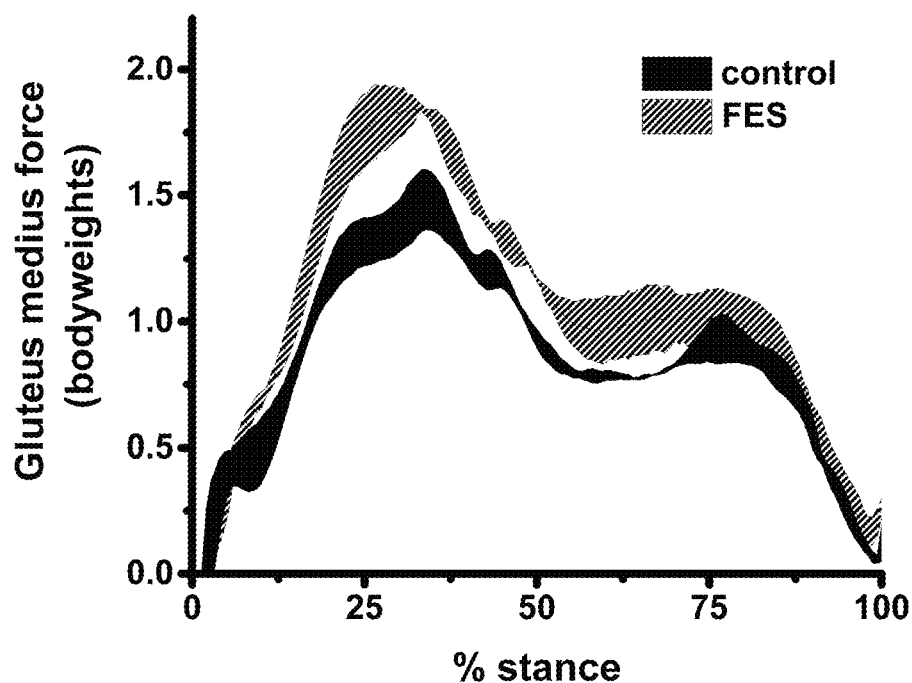
FIG. 1: Mean and standard error of gluteus medius force across trials for one subject in control and FES conditions

FES of the Gluteus Medius During Gait

The effects of specific muscular augmentation of gluteus medius on the medial knee JRF during level walking were investigated using motion capture and musculoskeletal modelling. Application of FES to gluteus medius facilitated an average reduction in the medial knee JRF AUC of 12.5%.

Methods

Motion Capture

The experimental setup for gait analysis comprised a set of 10 Vicon optoelectronic cameras (Vicon MX system, Vicon Motion Systems Ltd, Oxford, UK) trained on a level walkway with a force plate (Kistler Type 9286AA, Kistler Instrumente AG, Winterthur, Switzerland) at its centre 12 single infrared reflective markers and two 3-marker clusters were used to form a model of lower limb kinematics. For each subject recorded data included a single static trial, with the subject stood motionless in neutral posture, and multiple dynamic trials. During the latter, subjects walked normally across the walkway, taking several steps prior to landing with the right foot entirely on the force plate, and continuing for several steps thereafter; no instruction was given regarding walking speed. Data quality was contingent upon adequate marker visualization to allow reconstruction of relatively uninterrupted three-dimensional marker trajectories; only trials fulfilling this requirement were chosen for analysis.

Data Processing

Initial processing was performed using Vicon Nexus® (1.85) and Matlab® (2015a; The MathWorks Inc., Massachusetts, USA). A 4 Hz low-pass fourth order Butterworth filter was applied prior to data resampling, producing smoothed three-dimensional position data for all kinematic markers, and ground reaction force data, recorded at 200 Hz in a static general coordinate frame of reference. A musculoskeletal model, Freebody (1.1; Cleather D J, Bull AMJ. The development of a segment-based musculoskeletal model of the lower limb: Introducing FreeBody. Royal Society Open Science 2, (2015): 140449) was used to quantify muscle, joint and ligamentous forces for each sampled frame.

Simulation of Increased Gluteus Medius Activation

A dataset containing synchronously recorded kinematic (retro-reflective marker positions) and kinetic (ground reaction force) data during level walking was obtained by combining previously published data for six subjects with newly recorded data for a further six subjects Duffell et al. *Proceedings of the Institution of Mechanical Engineers, Part H: J Eng Med.* 2014; doi:10.1177/0954411913518747). Two separate optimisation routines were carried out for each dynamic trial: the first to reflect normal walking as the control condition, the second to simulate increased activation of gluteus medius through a manipulation of model parameters. For the former, the objective function used is described by:

$$\text{minimise } J = \sum_{i=1}^{n} \left(\frac{F_i}{F_{imax}}\right)^3; \quad (1)$$

(1), according to Crowninshield & Brand *J Biomech* 1981; 14(11):793-801) for the latter:

$$\text{minimise } J = \sum_{i=1}^{n} c \cdot \left(\frac{F_i}{F_{imax}}\right)^3 \quad (2)$$

$$c = \begin{cases} 0.25 & \text{gluteus medius} \\ 1 & \text{all other muscles} \end{cases}$$

where $F_i$ is the force output of the $i^{th}$ muscle element, $F_{imax}$ defines the $i^{th}$ muscle element's force at maximum contraction and n is the total number of muscle elements (163) . . . $F_{imax}$ is calculated for each element from peak cross-sectional area, which is determined using subject-specific measurements and anatomical dataset values. The method of simulating increased gluteus medius activity by use of a constant of value 0.25 is taken from a recent study showing appropriate increases in muscular activity with its application (unpublished observations, Xu R, and Bull A, described in Example 2).

Experimental Implementation of FES to Gluteus Medius
Healthy Subjects Participated Following completion of motion capture of normal walking trials as described above, the skin of the right gluteal region was prepared with 70% isopropyl alcohol skin wipes and FES gel electrodes (PALS® Platinum) were placed on the area overlying the right gluteus medius, along its line of action. The muscle was located by palpation, within the triangle formed by the right anterior superior iliac spine, right posterior superior iliac spine and the greater trochanter of the right femur. Gluteus maximus was avoided, as was the area superior to the iliac crest.

The electrodes were connected to a 2-channel electrode stimulator (OCHS II, Odstock Medical Limited, Salisbury, UK) limited to a maximum current of 80 mA, with asymmetrical biphasic current waveforms of frequency 45 Hz.

Effective electrode positioning was checked with the subject in left-legged stance: from an initial low setting, the applied current was increased stepwise until the limit of subject comfort was reached. Subjects walked down the gangway with electrodes in situ, and FES was activated prior to right foot strike such that stimulation was maximum for the period of right stance. After several trial runs during which the subject became accustomed to the required timing, motion capture commenced. Multiple trials were recorded.

Three control and three FES trials were taken for analysis from amongst the trials recorded towards the end of the session, to allow for adaptation to the imposed patterns of muscular activation. Freebody (1.1) was used to calculate muscle and joint reaction forces by application piecemeal to data from each trial. For control trials, the optimisation protocol employed equation (1) as the objective function. For FES trials, a modification was performed to account for the increased activation of gluteus medius, in a manner identical to that implemented in the preceding computer simulation, using equation (2) as the objective function.

Statistical Methods

Statistical analyses were performed using Matlab® (2015a). Time-integrated measures were determined using the trapezoidal method of numerical integration (Yeh & Kwan *J Pharmacokinet Pharmacodyn.* 1978; 6(1):79-98), and all forces and impulses were normalised to bodyweight to facilitate inter-subject comparison. Analysis was performed separately for each of two pre-defined phases of stance (mid-stance: 17 to 50% of stance and terminal-stance: 51 to 83%), and for the whole of stance. Components of the ground reaction force (GRF) were transformed into a local coordinate frame of reference defined by the evolving lower limb geometry in each frame, and areas under the curves (AUCs) were calculated for these transformed forces. Thus the vertical component was defined along the long axis of the tibia, the anteroposterior component by a vector perpendicular to this in the plane of the long axis of the foot, and the mediolateral component by a vector orthogonal to these two. In determining overall differences between control and FES trials for joint reaction and muscular forces, GRF components and kinematic parameters, normality of the underlying distributions was assumed and two-way analyses of variance (ANOVAs) with repeated measures were performed. These tests took all individual un-averaged trial data into account (two conditions with three repetitions for each, per subject), with nominal variables given by subject and condition (condition defined as control or FES). All reported p-values relate to differences between control versus FES trials; a significance threshold of p=0.05 was applied throughout. For inter-variable correlations Pearson's correlation coefficients were calculated (presented as R values) and for these p-values were determined by ANOVA.

Results
Modelling Simulation of FES

Optimisation of both types was successful for all trials of all 12 subjects, producing paired force outputs for every frame of each trial reflecting the control and FES-simulated conditions. An example is shown in FIG. 1. Modified optimisation routines to simulate an increased activation of gluteus medius resulted in a decrease in the medial knee JRF impulse for every trial of every subject (36 trials in total) when compared to the control condition. Total impulse was reduced by 4.2% on average (p=0.088) with a significant decrease in the magnitude of the mid-stance impulse (p=0.0001). Time-integrated muscular force generated by gluteus medius increased by 32% with FES simulation (p<0.0001).

Experimental Implementation of FES

Sixteen healthy subjects agreed to participate in the experimental protocol. One male subject was excluded on the basis of significant recent lower limb injury, leaving 15 who underwent testing (13 male, 2 female, age range 21 to 28, body mass index 21.6±2.5 kgm$^{-2}$). The range of stimulation currents tolerated by subjects varied from 31 mA to 80 mA (mean 52 mA). All participants tolerated FES well.

Figure 2:
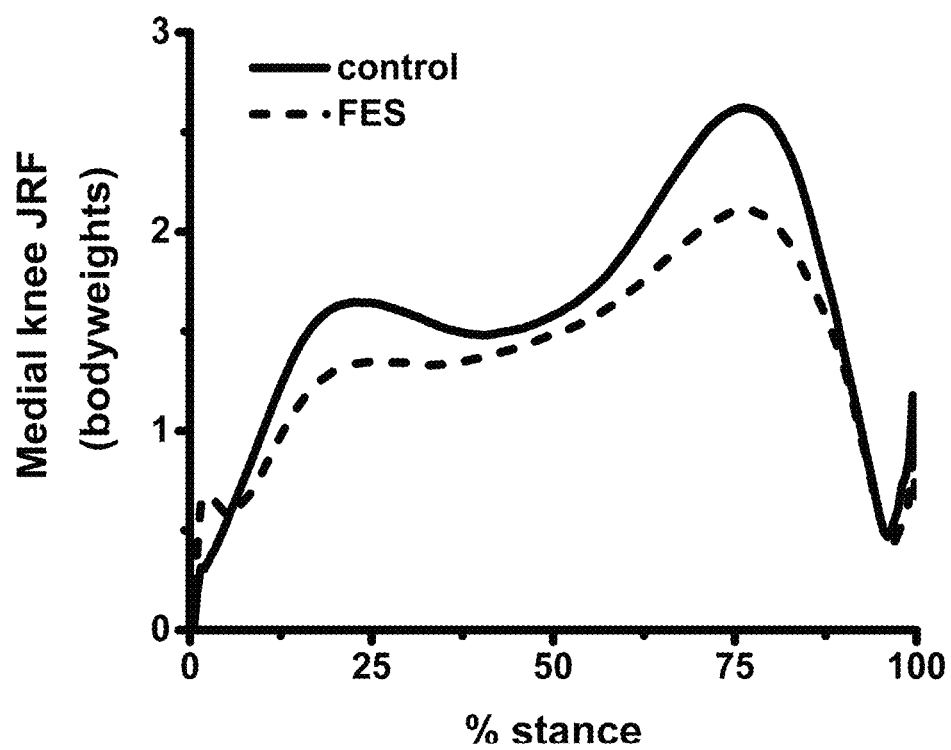
FIG. 2: Average trajectory of the medial knee JRF across all subjects and all trials in control and FES conditions

Medial Knee JRF 13 of 15 subjects showed reductions in the medial knee JRF impulse with FES. Overall, there were significant decreases at mid-stance ($p=8.3\times10^{-8}$), terminal stance) ($p=1.9\times10^{-10}$) and for the whole of stance ($p=5.6\times10^{-12}$). The average reduction in the total impulse across all subjects was 0.15 bodyweight-seconds, equivalent to a 12.5% decrease from control. Mean reductions in peak force with FES were 13.8% for the first peak and 18.4% for the second peak of the medial knee JRF ($p<0.0001$ in each case)(FIG. 2).

Muscular Forces

Average gluteus medius activity was 15% greater in FES trials compared control ($p<0.0001$).

Kinematics

Figure 3:
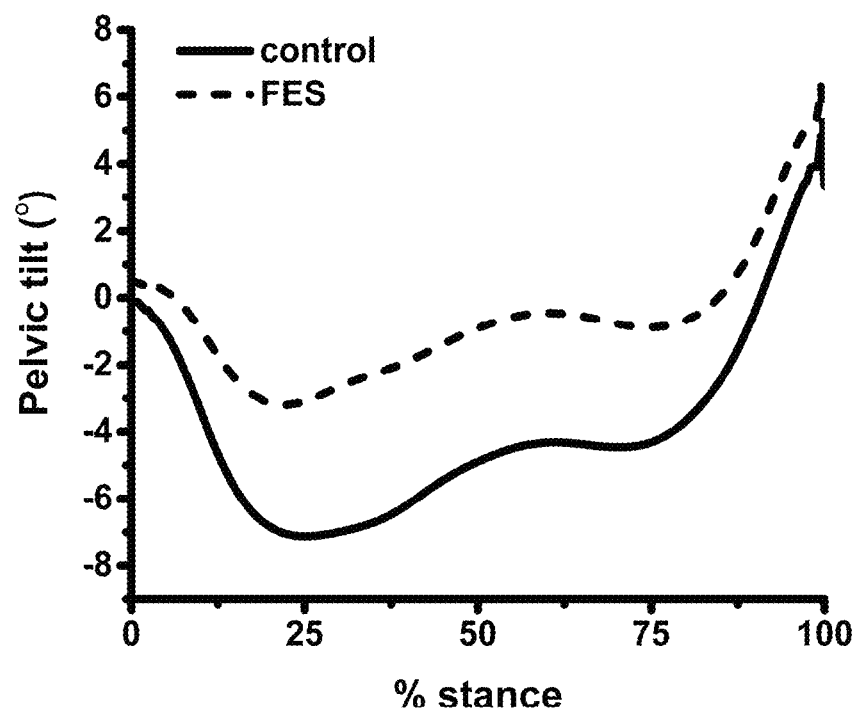
FIG. 3: Average trajectory of pelvic tilt angle in control and FES conditions. Negative values indicate pelvic drop below horizontal

Peak angle excursions were compared for selected joint angles, revealing widespread kinematic change in FES trials compared to control. In particular, peak pelvic drop below the horizontal was reduced by 46% ($p<0.0001$)(FIG. 3). Times to peak remained relatively unchanged.

Figure 5:
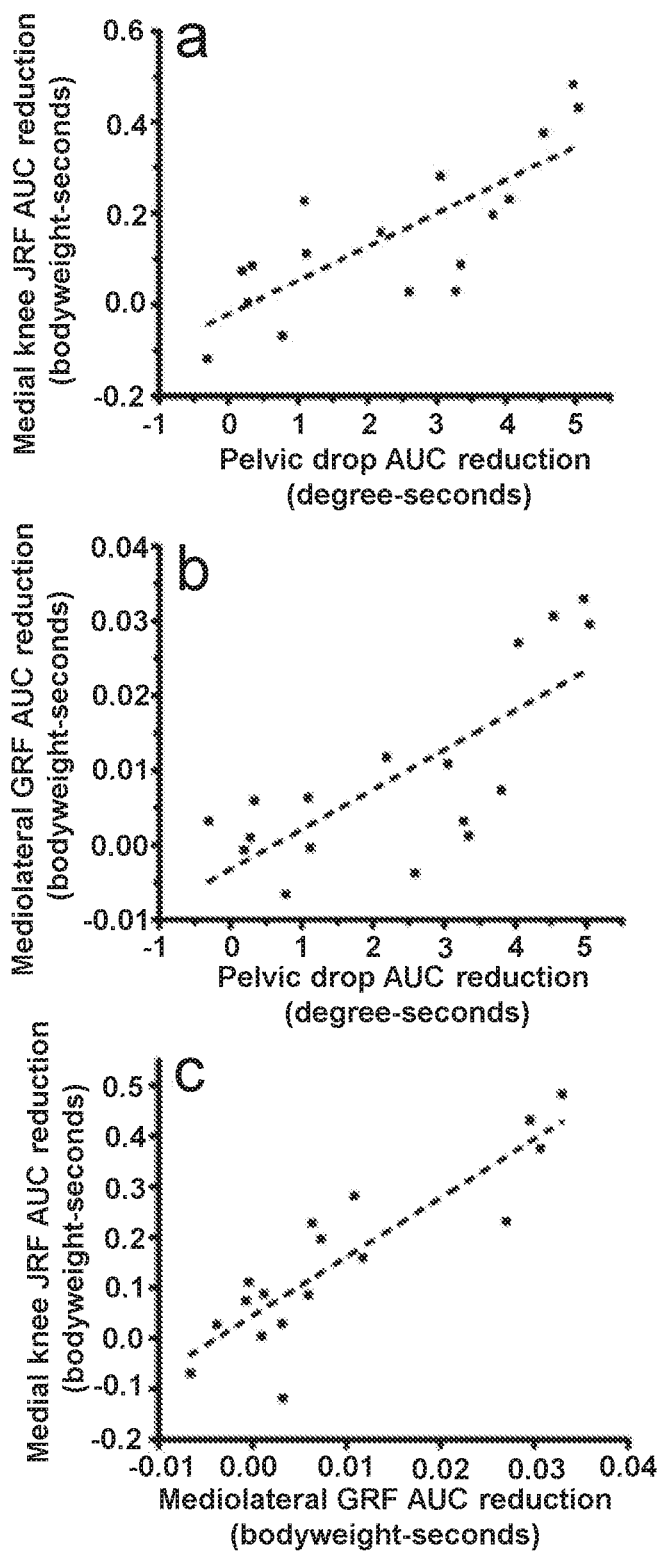
FIG. 5, Panel B: Reduction in pelvic drop versus reduction in mediolateral component of GRF (R=0.75, p=0.0005)

AUCs were computed for each joint angle, averaged within condition across all subjects and all trials. FES resulted in significant changes in AUC for pelvic tilt only ($p=0.0019$). Averaging belied a significant degree of inter-subject variation in kinematic parameters. The average reduction in pelvic drop AUC with FES was plotted against the average reduction in the medial knee JRF impulse, for each subject. Strong positive correlation was observed; see FIG. 5, Panel A.

Ground Reaction Force Components

Figure 4:
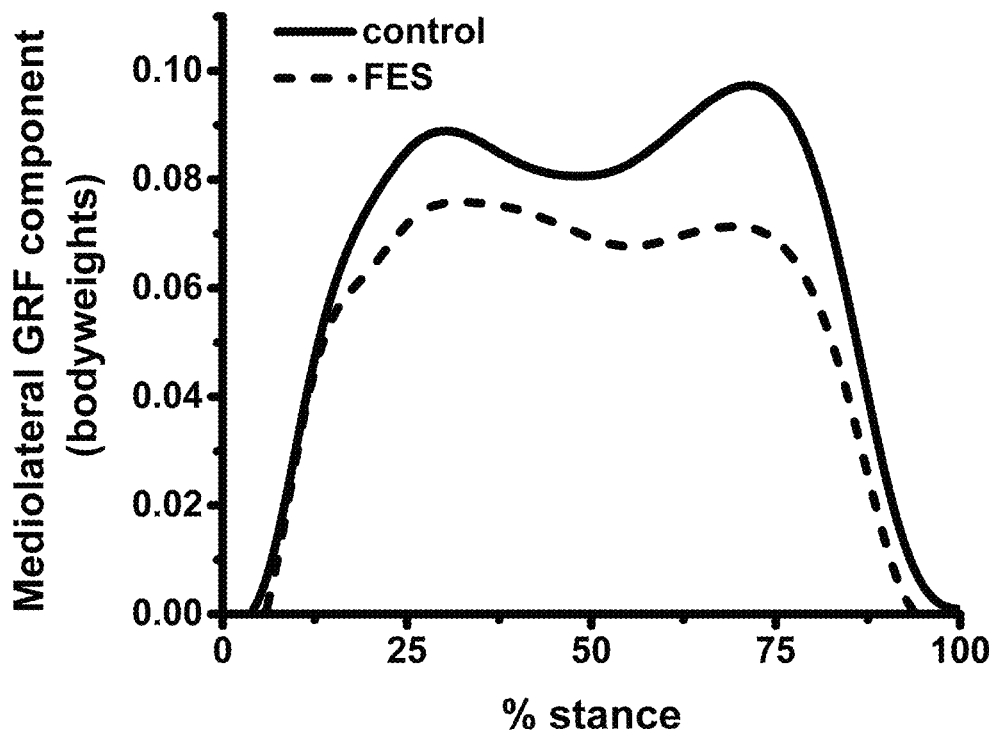
FIG. 4: Average trajectory of mediolateral component of GRF in control and FES conditions FIG. 5 (Panels A, B and C): Inter-variable correlations for change in pelvic tilt, mediolateral component of GRF and medial knee JRF impulse. All values represented in time-integrated form; each point represents data from a single subject. For two subjects who received FES with two different current levels, results from both have been plotted. Strong positive correlation was found across all variables FIG. 5, Panel A: Reduction in pelvic drop versus reduction in medial knee JRF (R=0.78, p=0.0002)

The mediolateral component AUC was reduced by 18% in FES trials compared to control ($p<0.0001$). In addition, there was a decrease in the vertical component ($p=0.05$) and an increase in the anteroposterior component ($p<0.0001$)(FIG. 4).

Significant inter-subject variation was observed in the degree of reduction of the mediolateral GRF component induced by FES in the local coordinate system. Plotting this reduction against the magnitude of reduction of pelvic tilt AUC for individual subjects revealed strong positive correlation. There was also strong positive correlation with the magnitude of reduction of the medial knee JRF impulse.

Discussion

The effects of specific muscular augmentation of gluteus medius on the medial knee JRF during level walking were investigated using motion capture and musculoskeletal modelling. Application of FES to gluteus medius facilitated an average reduction in the medial knee JRF AUC of 12.5%.

Crucially, across subjects, there were positive correlations between kinematic changes and changes to both the GRF and the medial knee JRF, with reductions in the latter scaling with both the extent of reduction of pelvic drop and the degree of lateralisation of the GRF. FES simulations using a single dataset (thus neglecting kinematic effects) grossly underestimated reductions in the medial knee JRF obtained with experimental implementation of FES (where kinematic changes were often profound). The following explanation is proposed: FES activates gluteus medius during stance, which through increased contraction reduces the extent to which the pelvis drops towards the swing leg. This effect lateralises the bodily centre of mass (shifting it towards the stance leg) and in doing so lateralises the GRF vector. Lateralisation of the GRF reduces its moment arm about the knee and thus the resultant varus torque, in turn reducing the medial compressive force and so the medial knee JRF.

This study shows the central importance of proper gluteus medius functioning for the protection of the knee and demonstrates the potential for intervention with FES to reduce the medial knee JRF in OA, particularly early OA. The mean values in reduction of peak medial knee JRF found here, of 13.8% and 18.4% for the first and second peak respectively, compare favourably with published reductions in the peak EAM following physiotherapy, where a mean reduction of 9% was observed and patients reported large reductions in pain scores following intervention (Thorp et al. *J Musculoskelet Neuronal Interact.* 2010; 10(2):166-173).

EXAMPLE 2

FES of the Biceps Femoris and Gastrocnemius During Gait

The effects of specific muscular augmentation of the long head of biceps femoris and lateral gastrocnemius on the medial knee JRF during level walking were investigated using motion capture and musculoskeletal modelling. Application of FES to the long head of biceps femoris and lateral gastrocnemius was investigated.

Methods

Experimental Data

Ten healthy subjects (age, 27.4±2.4 years; mass, 67.6±16.2 kg; height, 1.70±0.11 m; 5 males and 5 females) participated in this study and performed four gait tasks: normal walking, long head of biceps femoris (loBF), lateral gastrocnemius (latGAS) and vastus lateralis (VL) stimulated walking.

For normal walking, the subjects walked 6 trials at a self-selected speed; for FES-assisted walking, the subjects walked 6 trials first with loBF, then with the latGAS and lastly with the VL of the right leg stimulated. The electrode pads were put at the two motor points of the relevant muscles. The asymmetrical biphasic waveform was used with the maximum current of 60 mA (1 k ohm). The frequency of the pulse was set to 40 Hz as recommended by the FES manufacturer (Odstock 2 Channel Stimulator, Odstock Medical Ltd., UK). The pulse width was adjusted from 132.5 µs to 306.5 µs to generate visible muscle contraction at the limit of subjects' tolerance. The stimulation was started by a press of the foot switch and it lasted for 2 s to cover the whole of the stance phase of walking.

The same marker setup was used as for Example 1. The same motion capture and force plate system was used as for Example 1.

Modelling

The same musculoskeletal model was used as for Example 1

FES Simulation

The same cost function was used as in Example 1 (equation 2).

The muscle force will increase as long as the value of $c_s$ is less than 1. Conversely, increasing $c_s$ to greater than 1 will result in under activation of the muscle. As electrical stimulation recruits muscles directly, the combination of voluntary contractions with electrical stimulation produces stronger contraction (Martin et al. *Top Spinal Cord Inj Rehabil* 2012; 18(1):28-33). In order to explore the sensitivity of $c_s$ on the muscle and joint forces, varying values of $c_s$ (1, 0.75, 0.5, 0.25, 0.1 and 0) were implemented. Finally, $c_S$=0.25 was selected to simulate the FES stimulation.

The joint reaction forces in normal gait were calculated with the original cost function in (1); to investigate the effect of FES on kinematics and kinetics, the original cost function was also used for FES-assisted walking; to investigate the effect of optimising to increase muscle activation of the stimulated muscles, FESsim in (2) and (3) was also used for FES-assisted walking.

Statistical Analysis

Wilcoxon signed rank test (MATLAB, R2014a, The Mathworks, Inc, 2014) was used to determine if there was a significant difference between normal walking and FES-assisted walking. Muscle forces were compared to validate the effectiveness of FESsim. As two different cost functions were used and three muscles were stimulated, the loBF, latGAS and VL muscle forces in normal gait were compared with those forces during stimulated walking using both the original cost function and FESsim.

The absolute magnitude (in Body Weight—BW) and components of the knee medial forces (KMFs) in the tibial coordinate frame were compared between cases. Knee adduction moment is reported to be a surrogate of the KMF (Manal et al. *Osteoarthritis and Cartilage* 2015 23(7):1107-1111) and, is, therefore, also reported.

As FES is expected to also modify the resulting gait kinematics, so kinematics were also analysed. The joint angles are calculated as Euler angles based on the local coordinate systems of the adjacent segments (Dumas et al. *Comput Methods Biomech Biomed Engin.* 2004; 7(3):159-166). The angles were referenced to the standing posture at which the joint angles were defined to be zero. The sequence of angle calculation is first abduction/adduction, then external/internal rotation and lastly flexion/extension (plantar flexion/dorsiflexion for the ankle). The ranges (maximum and minimum values) of the ankle, knee and hip joint angles were calculated and compared in three dimensions for normal and FES stimulated walking tasks.

Maximal and minimal values of anterior and posterior GRF, and two peak values of lateral/medial and superior/inferior GRF during the stance phase were compared between normal gait and FES stimulated walking. Anonymised data files from the physical experiments and the computational simulations are available on request from the corresponding author.

In all analyses, each of the six trials per subject were analysed and then mean parameters presented.

Results

Sensitivity Analysis

Figure 6:
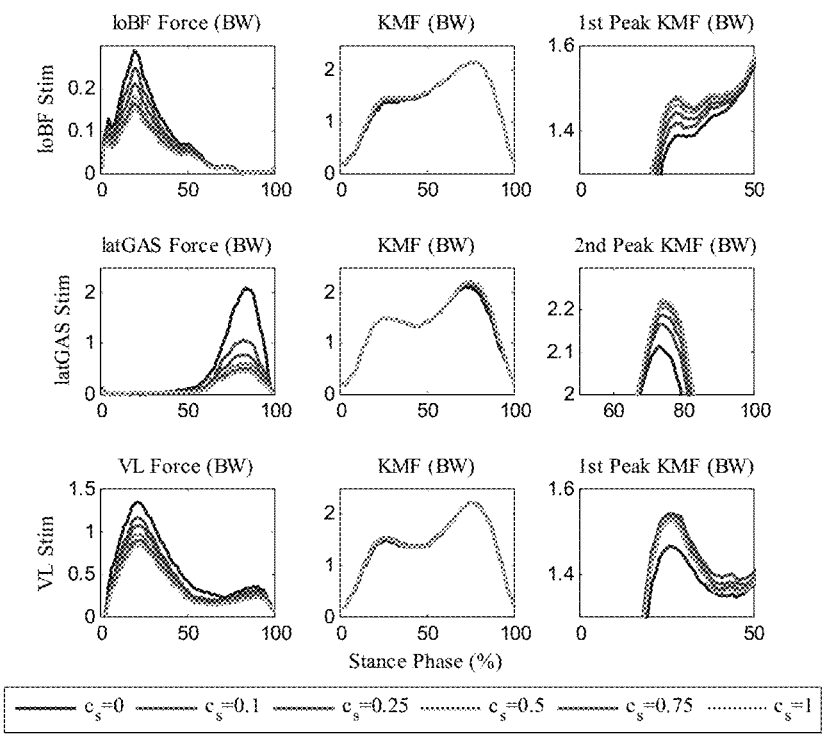
FIG. 6: Muscle forces and knee medial forces (KMFs) for varying $c_s$

The muscle forces and knee medial forces (KMFs) with varying $c_s$ for 10 subjects are plotted in FIG. 6. The stimulated muscle forces (including loBF, latGAS and VL forces) increase as $c_s$ decreases (first column of FIG. 6). The first peak of KMF decreases as the loBF force increases, the second peak of KMF decreases as the latGAS force increases and the VL has a similar effect with loBF on the first peak, but the decrease in KMF only became clearly apparent when $e_s$=0.

The $c_s$ values were chosen evenly between 0 and 1 (0, 0.25, 0.5, 0.75 and 1), where $c_s$=1 uses the original cost function (i.e. without additional stimulation). A value of $c_s$=0 assigns the greatest activation to the muscle. Where the muscles are not saturated (i.e. limited by their PCSA), $c_s$=0.25 for the stimulated muscle is equivalent to increasing the maximal force (or PCSA) of the stimulated muscle by a factor of 4; this assumes that extra motor units are available to be activated by FES. From another perspective, the use of c is to assume the stimulated muscle as a larger muscle which can produce stronger force according to the force-endurance relationship (Crowninshield & Brand *J Biomech* 1981; 14(11):793-801).

$c_s$=0.25 simulates a high activation of the stimulated muscle, but it does not saturate the muscle (one of the constraints requires the muscle force to be less than the maximal muscle force). Therefore, the muscle force with $c_s$=0.25 is expected to be achievable. Practically in the experiment, FES was used to contract the muscles at the maximum comfortable level for each subject.

Muscle Forces

Figure 7:
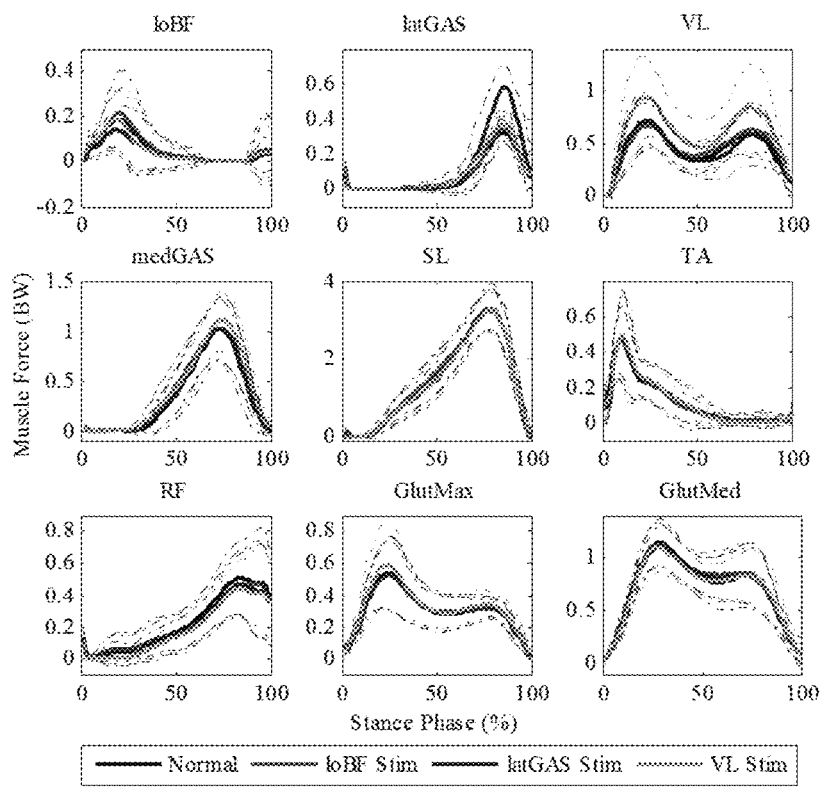
FIG. 7: Mean muscle forces obtained from FESsim (n=10). Solid line: mean values. Dashed line: standard deviations. Normal: normal walking; loBF Stim: loBF stimulated walking; latGAS Stim: latGAS stimulated walking; VL Stim: VL stimulated walking.

FIG. 7 depicts the mean forces of the main lower limb muscles of 10 subjects using FESsim during 4 tasks. The 9 muscles are loBF, latGAS, VL, medial head of GAS (medGAS), Soleus (SL), Tibialis Anterior (TA), Rectus Femoris (RF), Gluteus Maximus (GlutMax), and Gluteus Medius (GlutMed).

There was no significant difference in maximal muscle force values between normal gait and stimulated walking with the original cost function. However, maximal muscle force values in the stimulated tasks with FESsim were significantly larger than those in the normal task (Table I): the loBF force during loBF stimulation is significantly larger than that during normal walking, the latGAS force during latGAS stimulation is significantly larger than that during normal walking, the VL force during VL stimulation is significantly larger than that during normal walking.

TABLE I

Difference in maximal muscle forces of stimulated (using FESsim) and normal (using the original cost function) walking

| Muscle | Normal Walking Muscle forces (BW ± SD) | Difference in muscles forces for loBF Stimulated case (BW ± SD) | Difference in muscles forces for latGAS Stimulated case (BW ± SD) | Difference in muscles forces for VL Stimulated case (BW ± SD) |
|---|---|---|---|---|
| loBF | 0.22 ± 0.13 | 0.08 ± 0.09* | −0.01 ± 0.10 | 0.01 ± 0.10 |
| latGAS | 0.34 ± 0.07 | 0.03 ± 0.06 | 0.26 ± 0.09** | 0.04 ± 0.05 |
| VL | 0.76 ± 0.20 | −0.02 ± 0.12 | 0.03 ± 0.12 | 0.32 ± 0.16** |

(*p = 0.027;
**p = 0.002.

Positive value indicates increase and negative value indicates decrease).

The muscle forces for loBF, latGAS and VL found here are in agreement with the literature (Winby et al. *J Biomech* 2009 42(14):2294-2300): loBF is activated in early stance, latGAS in the stance and VL at the beginning and the end of the stance phase. The significant increase of stimulated muscle forces (Table I) guarantees the simulation of FES using FESsim.

The time of activation of loBF and latGAS during stance corresponds to the two KMF peaks. This should be the reason that loBF is stimulated to decrease the first peak and latGAS to decrease the second peak of the KMF (Table II).

TABLE II knee medial forces in BW (mean ± standard deviation)

| Task | Parameter | Original Cost Function | FESsim |
|---|---|---|---|
| Normal | 1st Peak | 1.41 ± 0.27 | 1.41 ± 0.27 |
|  | 2nd Peak | 2.12 ± 0.54 | 2.12 ± 0.54 |
| loBF Stim | 1st Peak | 1.39 ± 0.28 | 1.35 ± 0.28* |
|  | 2nd Peak | 2.10 ± 0.54 | 2.09 ± 0.55 |
| latGAS Stim | 1st Peak | 1.39 ± 0.28 | 1.39 ± 0.28 |
|  | 2nd Peak | 2.06 ± 0.50** | 2.04 ± 0.51# |
| VL Stim | 1st Peak | 1.41 ± 0.28 | 1.43 ± 0.29 |
|  | 2nd Peak | 2.09 ± 0.53 | 2.18 ± 0.54 |

(*P = 0.049;
**P = 0.020;
P = 0.006)

Figure 10:
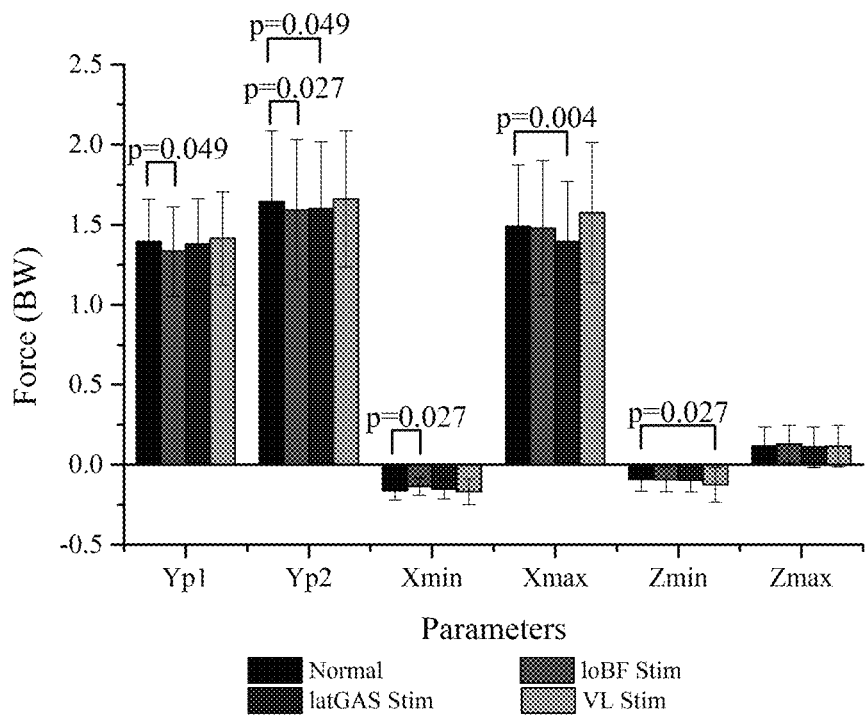
FIG. 10: Comparisons of KMF in x, y and z axes.

Yp1 and Yp2 are the two peak values of KMFy, Xmax and Xmin are the maximal and minimal KMF in the sagittal axis (KMFx) and Zmax and Zmin are the maximal and minimal KMF in the transverse axis (KMFz). These parameters were statistically compared between different cases. Results are shown in FIG. 10 and statistical differences were found for Yp1, Yp2 and Xmin during loBF stimulated walking, Yp2 and Xmax during latGAS stimulated walking, and Zmin during VL stimulated walking.

The knee lateral forces were also analysed to fully understand the effect of FES on the knee loading. There was no significant difference between the values during normal and stimulated walking.

Figure 12:
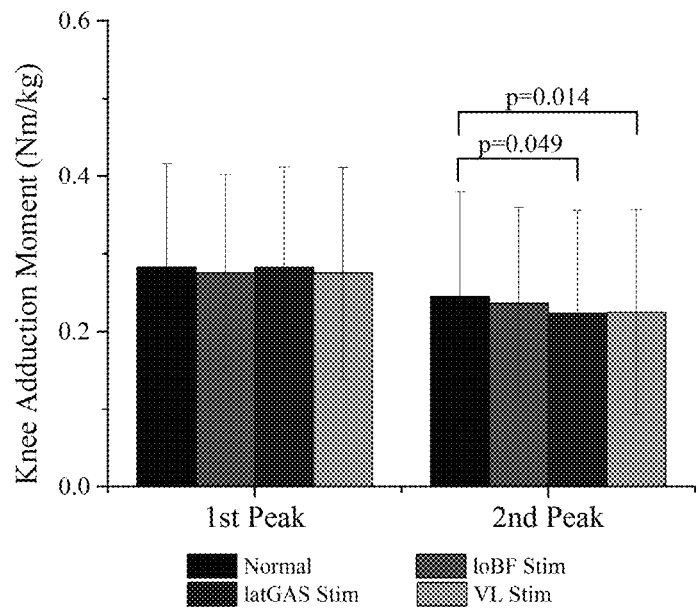
FIG. 12: Comparison of the knee adduction moment.

A computational study in the literature (Brandon et al. *J Biomech* 2014 47(6):1409-1415) found that stimulation of Vastus Lateralis and Biceps Femoris do not reduce the knee medial contact force. Our study is in agreement with the result for VL, but we found that loBF is able to reduce the KMF. A key difference between these studies is that they assumed that the kinematic and kinetic datasets remain the same for normal and stimulated walking. They did not stimulate the muscles and did not incorporate the changing kinematics and kinetics due to FES stimulation found here (FIG. 12 and Table III). It is therefore important to quantify the effect of stimulation on kinematics and kinetics.

TABLE III

Joint angle ranges (mean ± standard deviation) for FES stimulated and normal walking

| Joint | Angle | Normal | | loBF Stim | | latGAS Stim | | VL Stim | |
|---|---|---|---|---|---|---|---|---|---|
| | | Max | Min | Max | Min | Max | Min | Max | Min |
| Ankle | Abduction | 1.5 ± 1.8 | −8.4 ± 2.9 | 1.1 ± 1.4 | −9.2 ± 2.9 | 1.6 ± 2.2 | −9.0 ± 3.2 | 1.3 ± 1.5 | −8.9 ± 2.9 |
| | External Rotation | 9.0 ± 3.2 | −3.2 ± 2.9 | 9.5 ± 2.6 | −3.1 ± 2.5 | 9.8 ± 3.6* | −3.2 ± 3.2 | 9.5 ± 3.1 | −3.0 ± 2.4 |
| | Plantar Flexion | 13.3 ± 2.5 | −10.8 ± 4.2 | 13.6 ± 3.9 | −11.0 ± 4.2 | 12.4 ± 3.2 | −11.4 ± 4.3 | 13.0 ± 2.3 | −11.6 ± 4.3 |
| Knee | Abduction | 3.2 ± 1.3 | −1.0 ± 2.1 | 3.4 ± 1.4 | −0.7 ± 2.0 | 3.2 ± 1.2 | −1.0 ± 1.8 | 3.3 ± 1.4 | −1.0 ± 2.0 |
| | External Rotation | 3.1 ± 2.6 | −7.3 ± 4.0 | 3.5 ± 2.3 | −7.2 ± 3.5 | 2.6 ± 3.0 | −7.2 ± 3.7 | 3.0 ± 2.9 | −6.9 ± 3.1 |
| | Flexion | 41.0 ± 6.1 | 4.5 ± 5.1 | 40.8 ± 7.0 | 3.8 ± 4.4* | 39.6 ± 7.9 | 4.3 ± 5.8 | 41.3 ± 7.7 | 4.7 ± 5.9 |
| Hip | Abduction | 5.6 ± 3.8 | −7.2 ± 3.5 | 6.2 ± 3.5** | −7.2 ± 3.3 | 6.4 ± 3.7 | −7.0 ± 3.6 | 6.8 ± 4.3 | −7.0 ± 3.9 |
| | External Rotation | 4.6 ± 4.2 | −4.1 ± 3.7 | 4.1 ± 4.7 | −4.2 ± 3.8 | 3.9 ± 4.6 | −4.1 ± 3.6 | 3.7 ± 4.9 | −4.5 ± 4.5 |
| | Flexion | 9.8 ± 2.8 | −27.4 ± 4.5 | 9.9 ± 2.9 | −26.7 ± 5.2 | 9.2 ± 3.4 | −28.1 ± 6.7 | 9.0 ± 3.5 | −28.3 ± 5.8 |

(*P = 0.027;
**P = 0.049).

Knee Medial and Knee Lateral Forces

Figure 8:
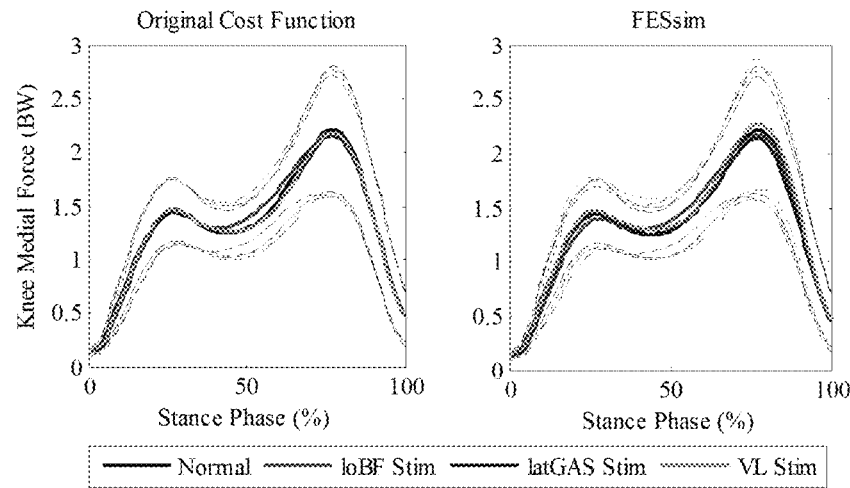
FIG. 8: Mean KMF obtained using the original cost function (Left) and FESsim (Right).

The mean KMFs are shown in FIG. 8. The KMF has two peaks during the stance phase occurring at 28% and 78% of the stance phase. The mean KMF of 20%-35% and 70%-85% of the stance phase are calculated to represent the two peak values. The second peak KMF in latGAS stimulated walking is decreased significantly using the original cost function (Table II); when using FESsim, the first peak in loBF stimulated walking and the second peak in latGAS stimulated walking are significantly smaller than that in normal walking.

Figure 9:
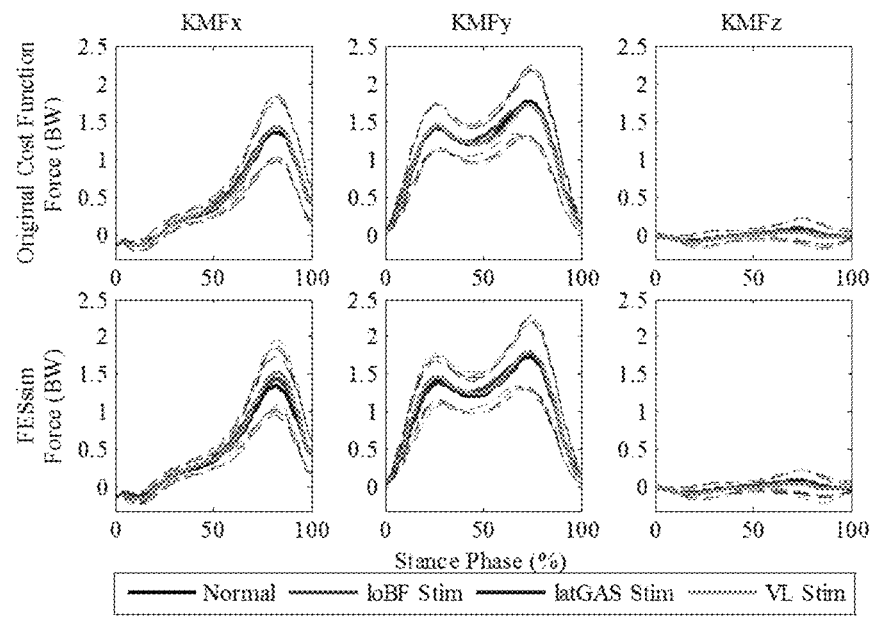
FIG. 9: Mean KMF in the x (anterior (+)-posterior (−) shear), y (superior (+)-inferior (−) compression) and z (lateral (+)-medial (−) shear) axes of the tibial coordinate frame obtained using the original cost function (top) and FESsim (bottom). Solid line: mean values. Dashed line: standard deviations.

FIG. 9 presents the components of the KMFs in different axes in the local coordinate system; peak values of the KMF in the longitudinal axis (KMFy) and knee adduction moment are calculated in the same way as for the overall KMF peak.

The shape of the KMF in stance phase has an expected double hump pattern with slightly higher peak than measured in-vivo. The literature has much information on the reasons for higher joint force predictions using musculoskeletal modelling; in this case, we hypothesise that such forces are appropriate due to our subjects being younger and more active than the in-vivo subjects with total joint replacements.

The mean of the second peak of the knee lateral forces are expected to increase as the lateral muscle forces are increased. However, there is no significant change in this parameter, thus giving the tantalising conclusion that a reduction in medial knee joint forces do not necessarily mean a concomitant increase in lateral forces at the knee.

Knee Adduction Moment

Figure 11:
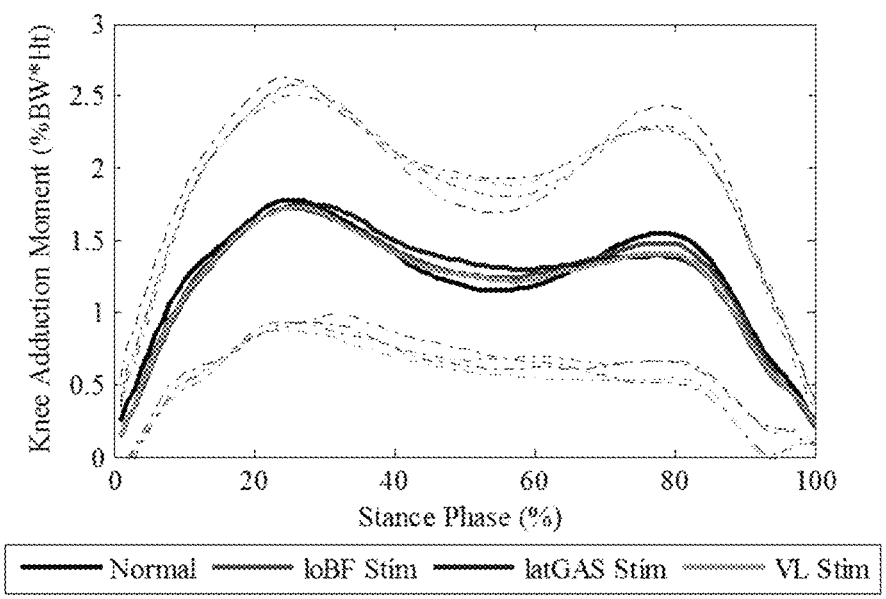
FIG. 11: Knee adduction moments. Solid line: mean values. Dashed line: standard deviations. BW*Ht: Body Weight×Height.

The average knee adduction moments are shown in FIG. 11. The second peak of the knee adduction moment during latGAS or VL stimulated walking is significantly smaller than that during normal walking (FIG. 12).

The knee moment curves shown in FIG. 11 are similar to those of Manal et al (Manal et al. *Osteoarthritis and Cartilage* 2015 23(7):1107-1111). The knee adduction moment is reported to be highly correlated with the medial contact force for different gait patterns and is thus often used as a surrogate measure (Zhao et al. *J Orthop Res* 2007 25(6):789-97).

The significant decrease in the second peak of this moment during latGAS stimulation is in accordance with the decrease in the KMF. However, the adduction moment does not detect a decrease in the first peak for loBF stimulated walking that was found here. The significant decrease in the second peak of the moment during VL stimulation does not reflect a decrease in the KMF.

Conclusion

This study demonstrates that it is possible to redistribute the knee loading and reduce the medial loading by strengthening and activating selected muscles across the healthy knee and this opens the door for prevention and alternative non-surgical interventions for knee OA.

EXAMPLE 3

Activation of Biceps Femoris Reduces Tibiofemoral Anterior Shear Force and Tibial Internal Rotation Torque This study tested the hypothesis that selective activation of the biceps femoris, one of the hamstrings muscles, can theoretically and practically reduce anterior tibial shear and tibial internal rotation torque at the knee. A combined modelling and experimental approach was taken.

Physical Experiments

The experiment was approved by the institutional ethics review board and written informed consent was obtained from all participants. 12 healthy subjects (5 male, 7 female; height 1.67±0.08 m; mass 66.74±16.80 kg; age 26.08±2.29 years) underwent walking activities without and with functional electrical stimulator (FES) electrodes (Odstock 2 Channel Stimulator, Odstock Medical Ltd., UK) placed over the BF. One electrode was placed at the bottom of the BF and one at the centre, with a distance of two hand widths between them. The frequency of the stimulator was set to 40 Hz as recommended by the FES manufacturer, and the intensity was adjusted to the maximum level that the subject was able to comfortably withstand. The subjects walked for six trials of which a random selection of three trials were used for data analysis. Internal rotation torque and anterior shear force at the knee were the measures of interest. Ground reaction forces (GRF) and motion were measured as in Examples 1 and 2.

Lower Limb Musculoskeletal model

The same musculoskeletal modelling software was used as in Examples 1 and 2

Optimisation Method

In order to quantify the effect of higher muscle activation of biceps femoris long head produced by the FES at the knee, a new optimisation method is proposed:

In the new optimisation method, the muscle force of biceps femoris is set as a constant value during the stance phase. This value is set at a muscle activation, c, times the maximum force of biceps femoris long head. As the attachment sites of biceps femoris long head are on the shank and thigh segments, the equations of motion of the shank and thigh segments were modified by the inclusion of an additional term to give:

$$\begin{bmatrix} \overline{S}_i \\ \overline{M}_i \end{bmatrix} = \begin{bmatrix} m_i E_{3\times3} & 0_{3\times3} \\ m_i \tilde{c}_i & I_i \end{bmatrix} \begin{bmatrix} \overline{a}_i - g \\ \ddot{\overline{\theta}}_i \end{bmatrix} + \begin{bmatrix} 0_{3\times1} \\ \dot{\overline{\theta}}_i \times I_i \dot{\overline{\theta}}_i \end{bmatrix} + \begin{bmatrix} E_{3\times3} & 0_{3\times3} \\ \tilde{d}_i & E_{3\times3} \end{bmatrix} \begin{bmatrix} \overline{S}_{i-1} \\ \overline{M}_{i-1} \end{bmatrix} - \begin{bmatrix} (c \times f_{BF_{max}}) \cdot \overline{n}_{BF} \\ (c \times f_{BF_{max}}) \cdot (\overline{r}_{BF_{tf}} \times \overline{n}_{BF}) \end{bmatrix}$$

where c is a constant, $f_{BF_{max}}$ the maximum force of long head biceps femoris, $\overline{n}_{BF}$ the line of action of long head biceps femoris and $\overline{r}_{BF_{tf}}$ the moment arm of long head biceps femoris. In this study, c was increased in increments of 0.05 until the peak anterior tibial shear was reduced to zero.

Data Analysis

The anterior shear force and internal rotation torque were averaged over three trials and presented as a mean value in the tibial coordinate frame. The stance phase was expressed in a 0-100% duration with a step interval of 1% using cubic spline data interpolation (MATLAB, the Mathworks Inc., Natick, USA). To test the hypothesis that the knee internal rotation torque and the anterior shear force was reduced by applying the FES over the biceps femoris long head, the difference between the internal rotational torque and the anterior tibial shear force calculated using gait data without FES and with FES were compared using a one-tail paired-samples t-test with an a level of 0.05 in MATLAB (The Mathworks Inc., Natick, Mass.).

Results

Figure 13:
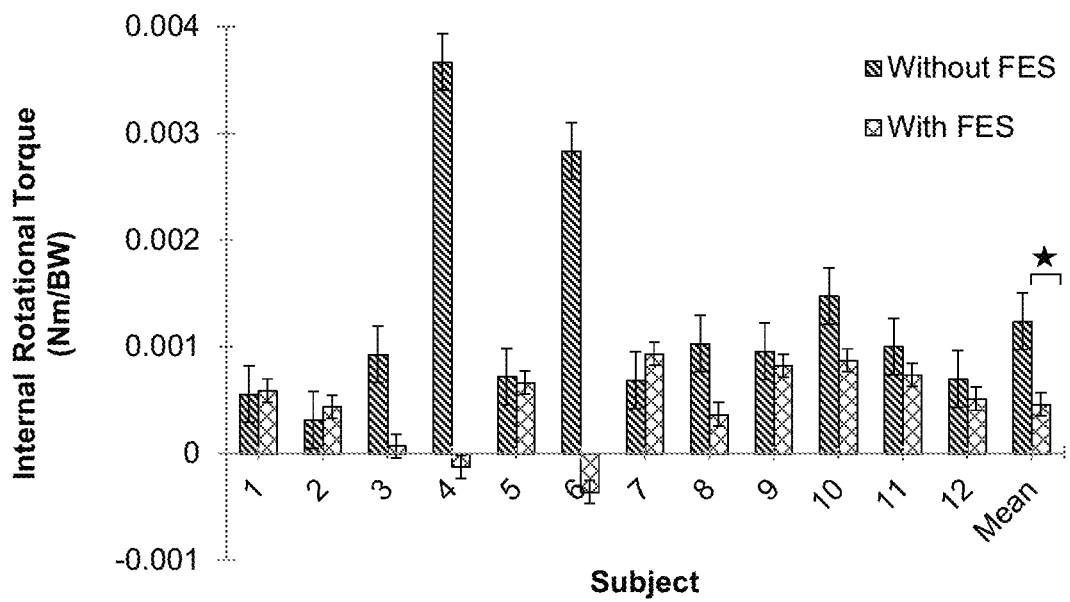
FIG. 13: Peak knee internal rotation torque for all subjects calculated in terms of two sets of gait data (*p<0.05) with standard optimisation.
Figure 14:
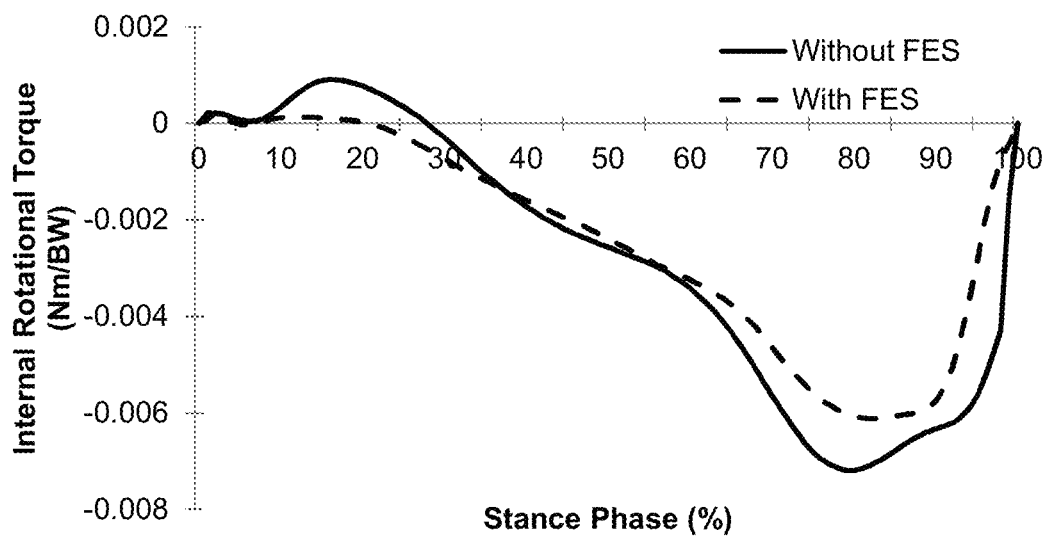
FIG. 14: Knee internal rotation torque of one representative subject for normal and FES gait with standard optimisation.
Figure 15:
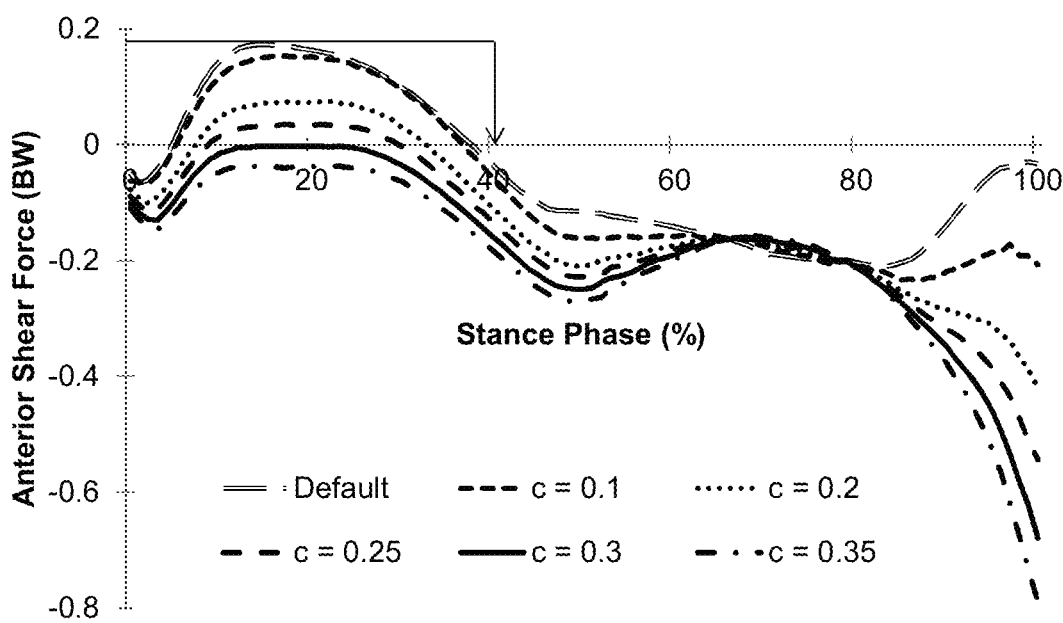
FIG. 15: Anterior shear force of one representative subject for the standard (c=0.104) and new optimisation methods (c=0.10, 0.20, 0.25, 0.30 & 0.35) for gait data without FES.
Figure 16:
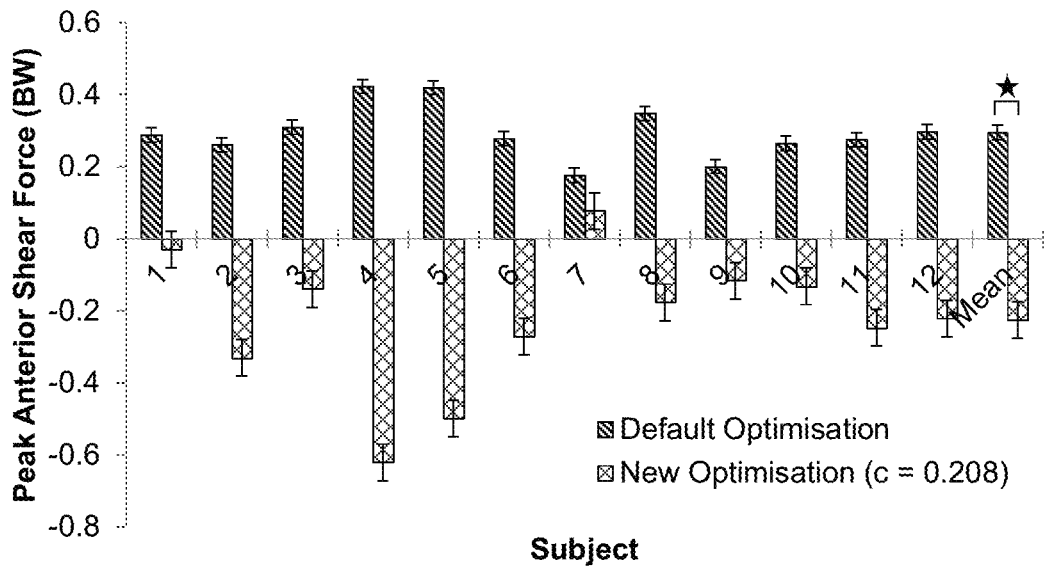
FIG. 16: A comparison of predicted peak anterior shear force during normal gait in the standard optimisation and in the new optimisation with a mean muscle activation, c, of 0.208.

The mean peak value of internal rotation torque at the knee during normal gait was 0.00124±0.00100 Nm/BW. The peak internal rotation torque was 63% smaller and reduced to 0.00046±0.00041 Nm/BW (p=0.032) with biceps femoris activation by FES (FIG. 13). FIG. 14 shows the internal torque at the knee for a representative subject.

Discussion

This study has tested the hypothesis that selective activation of the biceps femoris, one of the hamstrings muscles, can theoretically and practically reduce anterior tibial shear and tibial internal rotation torque at the knee. A combined modelling and experimental approach was taken.

The study found that the peak anterior shear force was significantly reduced when FES was applied. This is the first study to find that there was also a reduction in peak tibial internal rotation torque due to FES.

EXAMPLE 4

Gait Model Validation

The aim of this study is to validate a musculoskeletal model that quantifies and evaluates the effect of FES on selected muscles through measuring electromyography (EMG) of muscles that are not affected by the FES stimulation artefact. The hypothesis of this study is that FES-assisted activation of the biceps femoris long head (BFLH) during gait increases the activation of gluteus maximus, and that the EMG signals of gluteus maximus are clean from PES artefacts, because of its distance from the FES electrodes.

The hypotheses were tested through the application of three different current stimulation levels of FES to the BFLH of healthy subjects and through the simultaneous measurement of the EMG of gluteus maximus. Fifteen healthy subjects (6 males and 9 females; mean height 1.64±0.11 m; mass 64.0±12.0 kg; age 26.9±3.3 years) participated in the study. This study was approved by the institutional research ethics committee of Imperial College London and written informed consent was obtained from all participants.

Data Collection

Kinematic and kinetic data were captured in a motion analysis laboratory. Eighteen retro-reflective markers were placed on the pelvis and the right lower limb (Duffell et al. Proc Inst Mech Eng H. 2014; 228:206-10). Their trajectories were captured at 200 Hz using a ten-camera motion capture system (Vicon Motion Systems Ltd, Oxford, UK). Ground reaction forces of the right lower limb were measured at 1000 Hz from a force plate (Kitsler Type 9286BA, Kitsler Instrument AG, Winterthur, Switzerland). After six over ground walking trials, FES electrodes (Odstock 2 Channel Stimulator, Odstock Medical Ltd., UK) were placed on the subject's BFLH: one at the bottom and the other at the centre of the BFLH, with a distance of two hand widths between them. The level of FES pulse widths (μs) was set with an average level of three, according to subjects' tolerance towards the current stimulations. The frequency of the stimulator was 40 Hz, as recommended by the FES manufacturer, and the intensity was adjusted to the maximum level that each subject was able to comfortably withstand (Lynch & Popovic IEEE Contr Syst Mag. 2008; 28:40-50). Similar to the initial over ground walking trial, subjects walked in a self-selected comfortable speed with three FES stimulation currents, which were initialised at 40 mA and increased to 60 mA and finally to 80 mA. Walking trials were repeated six times at each current level. The stimulation current was set to start with one second of ramp up, followed by four seconds of maximum current level and then ending with one second of ramp down. The stimulator was manually started by the subject and timed so that the stimulation current was at its maximum value when the right foot stepped on the force plate, through the stages of heel strike and toe off.

Surface EMG sensors (Delsys, Trigno Wireless EMG System, USA) were placed according to SENIAM recommendations (Hermens et al. J Electromyogr Kines. 2000; 10:361-374) on the BFLH (the electrodes were placed halfway along the line between the ischial tuberosity and the lateral epicondyle of the tibia) and gluteus maximus (the electrodes were placed halfway along the line between the sacral vertebrae and the greater trochanter) of the right leg. The skin was treated with isopropyl alcohol prior to sensor application to ensure low impedance. For the first trial, an EMG sensor was attached over the BFLH. This was then replaced with the FES electrodes for the second and subsequent walking trials. Raw EMG data was band-pass filtered (30-300 Hz), whole wave rectified, and normalized to the maximum EMG signal of each particular subject (Buchanan et al. J Appl Biomech. 2004; 20:367-395).

Lower Limb Musculoskeletal Model

The same musculoskeletal modelling software was used as in Examples 1 and 2.

Optimisation Method

In order to simulate the effect of three FES current levels applied to BFLH, a modified optimisation method was used (Azmi et al. PLoS One. 2018; 13(1): e0190672). In this method, the muscle force of BFLH is set at a constant value during the stance phase which is equal to the muscle activation, c, times the maximum force of BFLH. As the attachment sites of BFLH are on the shank and thigh segments, the equations of motion of the shank and thigh segments were modified by the inclusion of an additional term to give:

$$\begin{bmatrix} S_i \\ M_i \end{bmatrix} = \begin{bmatrix} m_i E_{3\times 3} & 0_{3\times 3} \\ m_i c_i & I_i \end{bmatrix} \begin{bmatrix} a_i - g \\ \ddot{\theta}_i \end{bmatrix} +$$
$$\begin{bmatrix} 0_{3\times 1} \\ \dot{\theta}_i \times I_i \dot{\theta}_i \end{bmatrix} + \begin{bmatrix} E_{3\times 3} & 0_{3\times 3} \\ d_i & E_{3\times 3} \end{bmatrix} \begin{bmatrix} S_{i-1} \\ M_{i-1} \end{bmatrix} - \begin{bmatrix} (c \times f_{BFLH_{max}}) \cdot n_{BFLH} \\ (c \times f_{BFLH_{max}}) \cdot (r_{BFLH} \times n_{BFLH}) \end{bmatrix}$$

where c is a constant, $f_{BFLH_{max}}$ is the maximum force of BFLH, $n_{BFLH}$ is the line of action of BFLH and $r_{BFLH}$ is the moment arm of BFLH. The muscle forces of the remaining 162 muscles were re-optimised based on the modified equations of motion. In this study, the c value to present 40 mA, 60 mA and 80 mA current stimulations was set as 0.10, 0.15 and 0.20, respectively; these were all higher than the muscle activation of BFLH predicted from normal optimisation.

Data Analysis

Stance phase was expressed over a 0-100% duration with a step interval of 1%. This was then further divided into four sub-phases (Ardestani & Moazen J Biomech. 2016; 49:1620-1633): initial contact (0-3%), loading response (4-19%), mid stance (20-50%) and terminal stance (51-100%). The gluteus maximus activations predicted from the model and its EMG signals were averaged over three trials and presented as a mean value. Correlations of determination ($R^2$) were calculated between the predicted gluteus maximus muscle activations and its EMG data in terms of their peak values and the areas under the curve in each sub-phase of the stance.

Results

Figure 17:
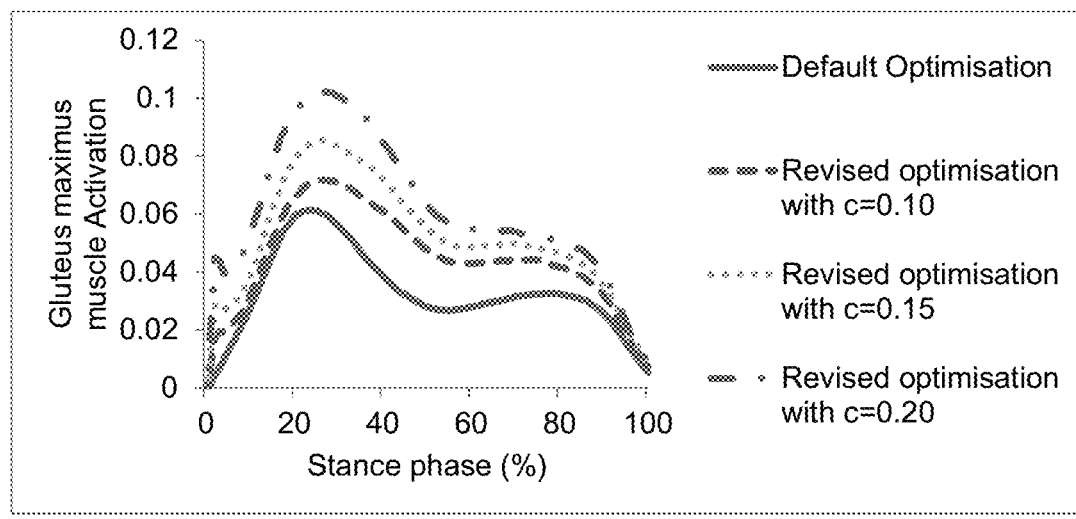
FIG. 17: Model predictions of gluteus maximus muscle activations (mean, n=15). Default optimisation refers to muscle activations during normal walking, and revised optimisation presents the muscle activations during FES applied walking.
Figure 18:
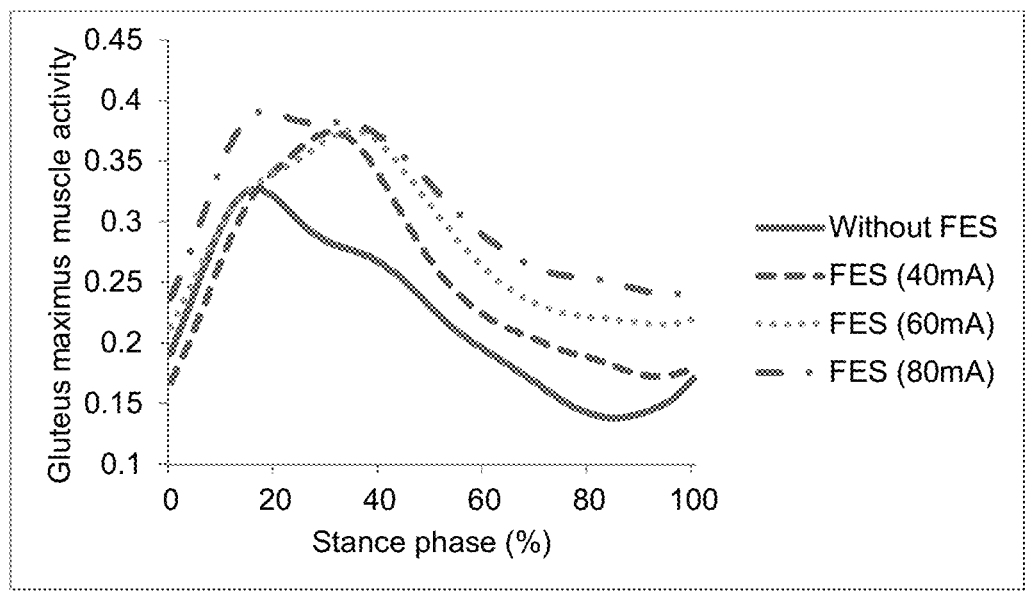
FIG. 18: Gluteus maximus EMG measurements (mean, n=15) in normal walking and FES applied walking

All subjects tolerated all tests at 40 mA and 60 mA stimulation. One subject did not tolerate 80 mA stimulation and therefore data at 80 mA are presented from 14/15 subjects. In normal walking and in FES applied walking, the gluteus maximus muscle activation predicted from models across all subjects is shown in FIG. 17 and its EMG measurement is shown in FIG. 18. Higher c values in the optimisation function contribute to greater gluteus maximus activation. A similar trend of its activity was found from the measured EMG (FIG. 18).

Figure 19:
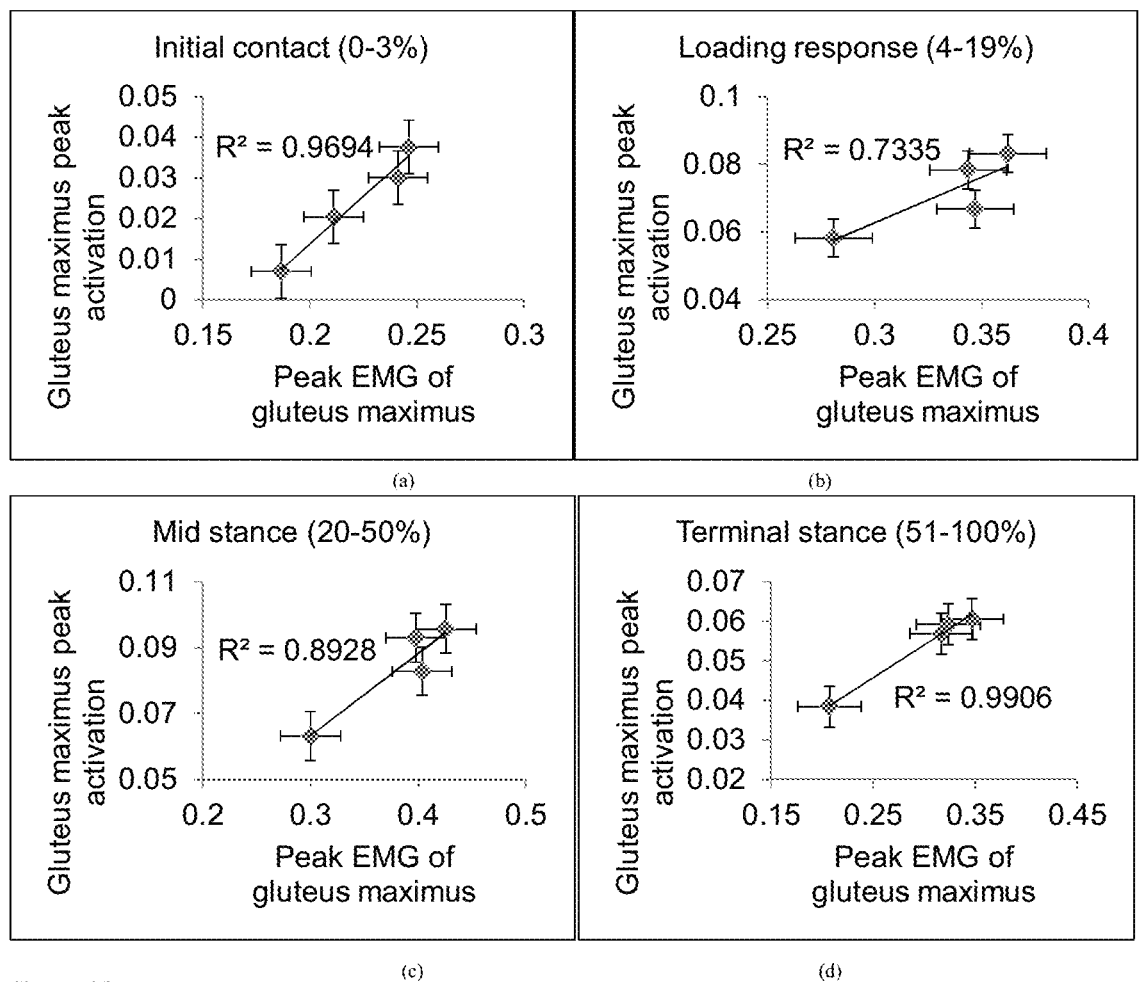
FIG. 19: Correlations between predicted peak gluteus maximus activation and its measured peak EMG signals in each sub-phase of the stance phase: initial contact (a), loading response (b), mid stance (c) and terminal stance (d). The four datapoints in each graph represent normal walking, and FES applied walking with FES currents of 40 mA, 60 mA and 80 mA.

Predicted peak activation and maximum EMG measurement of the gluteus maximus are highly correlated, with the $R^2$ values ranging from 0.73 to 0.96 (FIG. 19, Table IV; $R^2$=0.73-0.99).

TABLE IV

Peak gluteus maximus activations calculated by musculoskeletal modelling and as measured by EMG during the stance phase of normal walking and FES applied walking. c values of 0.10, 0.15 and 0.20 in models represent FES currents of 40 ma, 60 ma and 80 ma, respectively (mean ± sd, n = 15).

Peak Gluteus Maximus

| Stance phase (%) | Model predictions | | | | EMG | | | |
|---|---|---|---|---|---|---|---|---|
| | No FES | c = 0.10 | c = 0.15 | c = 0.20 | No FES | 40 mA | 60 mA | 80 mA |
| 0-3% | 0.01 ± 0.01 | 0.02 ± 0.01 | 0.03 ± 0.02 | 0.04 ± 0.03 | 0.19 ± 0.15 | 0.21 ± 0.17 | 0.24 ± 0.17 | 0.25 ± 0.19 |
| 4-19% | 0.06 ± 0.02 | 0.07 ± 0.02 | 0.08 ± 0.02 | 0.08 ± 0.04 | 0.28 ± 0.17 | 0.35 ± 0.21 | 0.34 ± 0.17 | 0.36 ± 0.20 |
| 20-50% | 0.06 ± 0.02 | 0.08 ± 0.26 | 0.09 ± 0.02 | 0.10 ± 0.04 | 0.30 ± 0.17 | 0.40 ± 0.19 | 0.40 ± 0.20 | 0.43 ± 0.23 |
| 51-100% | 0.04 ± 0.14 | 0.06 ± 0.02 | 0.06 ± 0.01 | 0.06 ± 0.02 | 0.21 ± 0.14 | 0.32 ± 0.18 | 0.32 ± 0.15 | 0.35 ± 0.23 |

Figure 20:
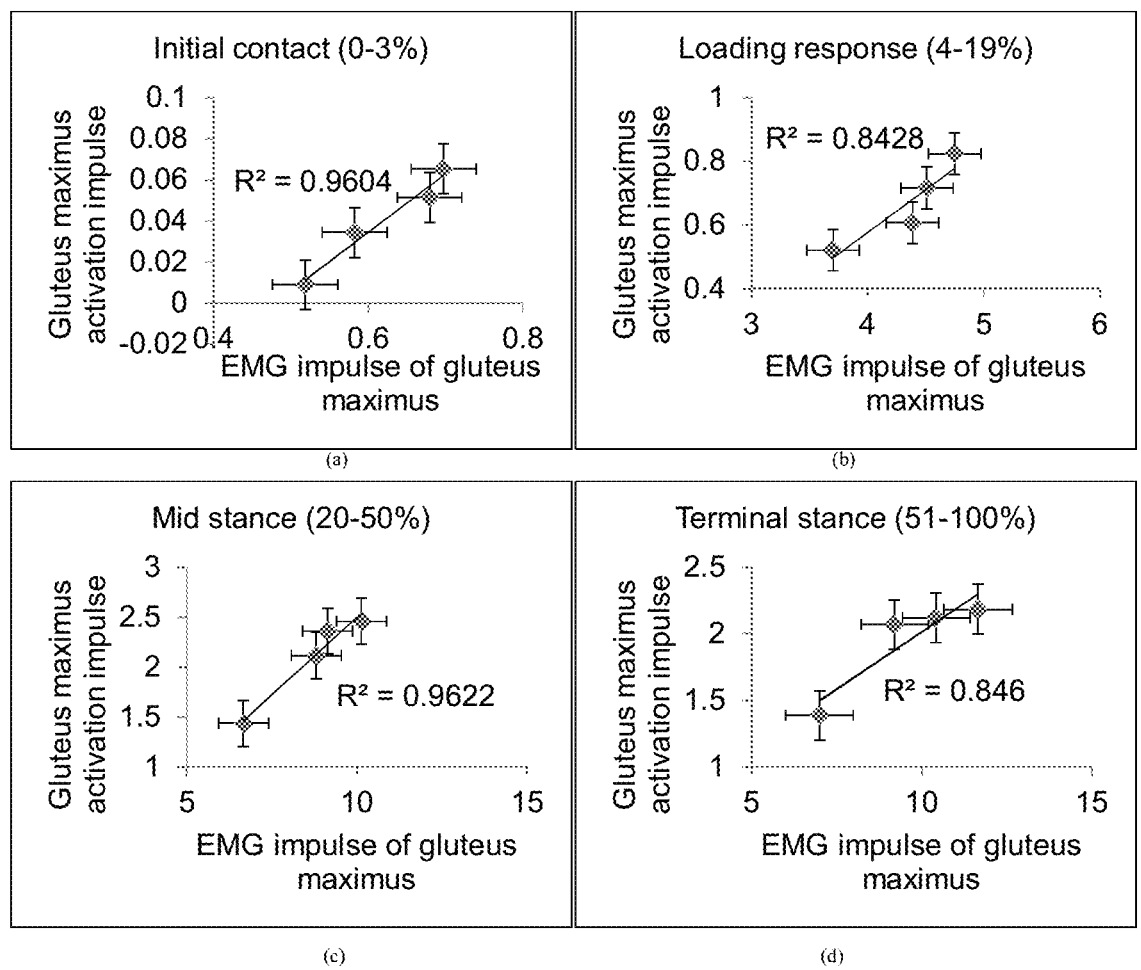
FIG. 20: Correlations between predicted gluteus maximus activation impulse (area under the curve) and measured EMG impulse in each sub-phase of the stance phase: initial contact (a), loading response (b), mid stance (c) and terminal stance (d). The four datapoints in each graph represent normal walking, and FES applied walking with FES currents of 40 mA, 60 mA and 80 mA.

Predicted gluteus maximus activation impulse and measured EMG impulse were highly correlated, with the $R^2$ values ranging from 0.84 to 0.96 (FIG. 20, Table V).

TABLE V

Gluteus maximus activation impulse calculated by musculoskeletal modeling and as measured by EMG during the stance phase of normal walking and FES applied walking. c values of 0.10, 0.15 and 0.20 in models represent FES currents of 40 ma, 60 ma and 80 ma, respectively (mean ± sd, n = 15)

Impulse (area under the curve)

| Stance phase (%) | Model predictions | | | | EMG | | | |
|---|---|---|---|---|---|---|---|---|
| | No FES | c = 0.10 | c = 0.15 | c = 0.20 | No FES | 40 mA | 60 mA | 80 mA |
| 0-3% | 0.01 ± 0.01 | 0.03 ± 0.02 | 0.05 ± 0.03 | 0.07 ± 0.05 | 0.52 ± 0.41 | 0.58 ± 0.47 | 0.68 ± 0.50 | 0.70 ± 0.53 |
| 4-19% | 0.52 ± 0.16 | 0.61 ± 0.22 | 0.72 ± 0.26 | 0.82 ± 0.39 | 3.70 ± 2.50 | 4.39 ± 3.11 | 4.51 ± 2.47 | 4.75 ± 2.82 |
| 20-50% | 1.44 ± 0.40 | 2.11 ± 0.67 | 2.36 ± 0.52 | 2.46 ± 0.71 | 6.66 ± 3.92 | 8.81 ± 4.37 | 9.14 ± 5.06 | 10.13 ± 5.02 |
| 51-100% | 1.39 ± 0.49 | 2.07 ± 0.87 | 2.12 ± 0.60 | 2.18 ± 0.66 | 7.00 ± 4.22 | 9.20 ± 3.78 | 10.42 ± 5.99 | 11.66 ± 8.01 |

Discussion

This study has experimentally validated an algorithm implemented in a musculoskeletal model to simulate the effect of FES stimulation and has shown that FES-assisted activation of BFLH during gait proportionally increases the activation of gluteus maximus.

Gluteus maximus, together with gastrocnemius, are the muscles which compensate for weakness of the BF to restore control at the hip during stance phase (Jonkers et al. Gait Posture. 2003; 17:264-272). Other studies have shown that the primary compensatory muscles for hamstrings weakness are gluteus maximus, three-component vasti (Komura & Nagano J Biomech. 2004; 37:425-36) and iliacus psoas (Ardestani & Moazen J Biomech. 2016; 49:1620-1633). In this study, the gluteus maximus was chosen for two reasons: it is positioned at a distance from BFLH and it shares function with BF as a hip extensor (Kendall et al. "Muscles: Testing and Function with Posture and Pain" 5th ed. 1993 USA: Lippincott William & Wilkins; Perry & Burnfield "Gait Analysis: Normal and Pathological Function" 2nd ed. 2010 USA: SLACK Inc.). This study found that FES artefact signals from the stimulated BFLH did not affect the EMG readings at gluteus maximus.

Both mean peak gluteus maximus muscle activation predicted from the models and mean peak gluteus maximus activity from EMG measurement occurred during mid stance (20-50% of stance phase; Table IV); prior work has also shown that this takes place in mid stance (Winter & Yack Electroen Clin Neuro. 1987; 67:402-411).

In this study, the musculoskeletal modelling cost function was modified from its standard form by assigning and weighting a variable, c, to simulate the BFLH as previously presented in the literature (Azmi et al. PLoS One. 2018; 13(1):e0190672). In a previous study, the value of c for each subject that reduced anterior shear force to zero was found and the mean value of c across all subjects was 0.208 for 40 mA FES current stimulation (Azmi et al. PLoS One. 2018; 13(1):e0190672). In this study, the FES current stimulation was set to three different levels. The c values chosen for the FES gait set of 40, 60 and 80 mA were 0.10, 0.15 and 0.20 respectively. These were chosen to mimic the incremental increase in BFLH activation caused by the different levels of FES current stimulation. The incremental increase in BFLH activation was found from the increasing EMG signals of the gluteus maximus.

The good correlations between peak and impulse of gluteus maximus activation between modelling and EMG signals (FIG. 19; FIG. 20) provide strong validation for the algorithm used in the musculoskeletal model and show that FES stimulation can be tuned to a level to achieve different outcomes. This dose-response relationship can be harnessed for clinical benefit in many different lower limb pathologies.

The literature highlights that during loading response, when the hamstrings action is reduced, the gluteus maximus activity should be increased to provide hip stability (Perry & Burnfield "Gait Analysis: Normal and Pathological Function" 2nd ed. 2010 USA: SLACK Inc.). Interestingly, in the study shown here, gluteus maximus activity increased with increasing activation of the BF using FES during walking. This increased activity of the gluteus maximus activity occurred because the BFLH and gluteus maximus actions are multi joint processes. The gluteus maximus and hamstrings are the hip extensor and knee flexors respectively and have increasing activity in late swing to control the forward movement of the swinging lower limb (Winter & Yack Electroen Clin Neuro. 1987; 67:402-411). Moreover, the hip extensor muscles have two functions, firstly to decelerate the limb's momentum in terminal swing to prepare for stance, and secondly to restrain the forward momentum of the pelvis and trunk as the limb is loaded (Perry & Burnfield "Gait Analysis: Normal and Pathological Function" 2nd ed. 2010

USA: SLACK Inc.). In addition, during stance phase, the primary muscles controlling the hip are the extensors and abductors, which include the gluteus maximus. The extra activation of the BFLH with FES in this study forced gluteus maximus activity to be activated from late mid swing through the loading response more than usual. As the hamstrings and gluteus maximus have a complementary role as the plantar flexors, this might also change not only the kinematics of the foot (Jonkers et al. Gait Posture. 2003; 17:264-272) but also of the knee and hip during early stance phase. Both BFLH and gluteus maximus also assist in lateral rotation of the tibia. These multi-joint actions provide an explanation for why the extra activation of BFLH with FES contributes to such large changes to gluteus maximus muscle activity.

Conclusion

This study is the first investigation to show how the activation of the BFLH correlates with the muscle activity of the gluteus maximus. The results from this study also validate a musculoskeletal modelling method that can simulate functional electrical stimulation during gait. This musculoskeletal model can be used to predict muscle activation for any clinical study using FES.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. A method of treating medial knee joint pain during gait in a patient in need thereof, the method comprising the following steps during gait:
   a) applying functional electrical stimulation to one or more of the gluteus medius, biceps femoris or gastrocnemius of the leg in need of treatment prior to foot strike of the foot of the leg in need of treatment;
   b) maintaining functional electrical stimulation to the muscle(s) stimulated in step a) for the period of stance of the leg in need of treatment;
   c) ceasing functional electrical stimulation of the muscle stimulated in step a) at the end of the period of stance of the leg in need of treatment;
   d) optionally repeating steps a) to c) in respect of the corresponding muscle(s) of the patient's other leg; and
   e) repeating steps a) to d) for each stride of the patient.

2. The method of claim 1, comprising applying sufficient functional electrical stimulation to one or more of the gluteus medius, biceps femoris or gastrocnemius to achieve a leg abduction angle of from 30° to 45°.

3. The method of claim 1, wherein the functional electrical stimulation is applied to the gluteus medius.

4. The method of claim 1, wherein the functional electrical stimulation is applied to the biceps femoris.

5. The method of claim 4, wherein the functional electrical stimulation is applied to the long head of the biceps femoris.

6. The method of claim 1, wherein the functional electrical stimulation is applied to the gastrocnemius.

7. The method of claim 6, wherein the functional electrical stimulation is applied to the lateral gastrocnemius.

8. The method of claim 1, wherein the patient is human.

9. The method of claim 1, wherein the patient suffers from osteoarthritis in the knee.

10. A method of treating or preventing osteoarthritis of the knee joint in a patient in need thereof, the method comprising the following steps during gait:
    a) applying functional electrical stimulation to one or more of the gluteus medius, biceps femoris or gastrocnemius of the leg in need of treatment prior to foot strike of the foot of the leg in need of treatment;
    b) maintaining functional electrical stimulation to the muscle(s) stimulated in step a) for the period of stance of the leg in need of treatment;
    c) ceasing functional electrical stimulation of the muscle stimulated in step a) at the end of the period of stance of the leg in need of treatment;
    d) optionally repeating steps a) to c) in respect of the corresponding muscle(s) of the patient's other leg; and
    e) repeating steps a) to d) for each stride of the patient.

11. The method of claim 10, comprising applying sufficient functional electrical stimulation to one or more of the gluteus medius, biceps femoris or gastrocnemius of up to 150 mA, preferably from 5 to 80 mA.

12. The method of claim 10, wherein the functional electrical stimulation is applied to the gluteus medius.

13. The method of claim 10, wherein the functional electrical stimulation is applied to the biceps femoris.

14. The method of claim 13, wherein the functional electrical stimulation is applied to the long head of the biceps femoris.

15. The method of claim 10, wherein the functional electrical stimulation is applied to the gastrocnemius.

16. The method of claim 15, wherein the functional electrical stimulation is applied to the lateral gastrocnemius.

17. The method of claim 1, wherein the patient is human.

18. A method of treating knee instability during gait in a patient with an anterior cruciate ligament deficiency, the method comprising the following steps during gait:
    a) applying functional electrical stimulation to the biceps femoris of the leg having an anterior cruciate ligament deficiency, prior to foot strike of the foot of said leg;
    b) maintaining functional electrical stimulation to the biceps femoris for the stance period of said leg;
    c) ceasing functional electrical stimulation of the biceps femoris at the end of the stance period of said leg;
    d) optionally repeating steps a) to c) in respect of the patient's other leg; and
    e) repeating steps a) to d) for each stride of the patient.

19. The method of claim 18, wherein the patient is human.

* * * * *